US010633625B2

(12) United States Patent
Nankervis et al.

(10) Patent No.: US 10,633,625 B2
(45) Date of Patent: *Apr. 28, 2020

(54) EXPANDING CELLS IN A BIOREACTOR

(71) Applicant: Terumo BCT, Inc., Lakewood, CO (US)

(72) Inventors: Brian J. Nankervis, Thornton, CO (US); Mark E. Jones, Littleton, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/542,304

(22) Filed: Nov. 14, 2014

(65) Prior Publication Data
US 2015/0140654 A1 May 21, 2015

Related U.S. Application Data

(60) Provisional application No. 61/905,182, filed on Nov. 16, 2013.

(51) Int. Cl.
| C12M 1/00 | (2006.01) |
| C12M 3/04 | (2006.01) |
| C12M 1/12 | (2006.01) |
| C12M 1/36 | (2006.01) |
| C12N 5/0775 | (2010.01) |

(52) U.S. Cl.
CPC ............ *C12M 29/18* (2013.01); *C12M 23/50* (2013.01); *C12M 25/10* (2013.01); *C12M 25/12* (2013.01); *C12M 27/10* (2013.01); *C12M 29/10* (2013.01); *C12M 29/16* (2013.01); *C12M 41/48* (2013.01); *C12N 5/0663* (2013.01)

(58) Field of Classification Search
CPC ...... C12M 29/18; C12M 23/50; C12M 25/10; C12M 25/12; C12M 27/10; C12M 29/10; C12M 29/16; C12M 41/48; C12N 5/0663
See application file for complete search history.

(56) References Cited

U.S. PATENT DOCUMENTS

| 3,821,087 A | 6/1974 | Knazek et al. |
| 3,883,393 A | 5/1975 | Knazek et al. |
| 3,896,061 A | 7/1975 | Tanzawa et al. |
| 3,997,396 A | 12/1976 | Delente |
| 4,184,922 A | 1/1980 | Knazek et al. |
| 4,200,689 A | 4/1980 | Knazek et al. |
| 4,220,725 A | 9/1980 | Knazek et al. |
| 4,391,912 A | 7/1983 | Yoshida et al. |
| 4,439,322 A | 3/1984 | Sonoda et al. |
| 4,647,539 A | 3/1987 | Bach |
| 4,650,766 A | 3/1987 | Harm et al. |
| 4,657,866 A | 4/1987 | Kumar |
| 4,722,902 A | 2/1988 | Harm et al. |
| 4,804,628 A | 2/1989 | Cracauer et al. |
| 4,885,087 A | 12/1989 | Kopf |
| 4,889,812 A | 12/1989 | Guinn et al. |
| 4,894,342 A | 1/1990 | Guinn et al. |
| 4,918,019 A | 4/1990 | Guinn |
| 4,973,558 A | 11/1990 | Wilson et al. |
| 4,999,298 A | 3/1991 | Wolfe et al. |
| 5,079,168 A | 1/1992 | Amiot |
| 5,126,238 A | 6/1992 | Gebhard et al. |
| 5,162,225 A | 11/1992 | Sager et al. |
| 5,192,553 A | 3/1993 | Boyse et al. |
| 5,202,254 A | 4/1993 | Amiot |
| 5,330,915 A | 7/1994 | Wilson et al. |
| 5,397,706 A | 3/1995 | Correa et al. |
| 5,399,493 A | 3/1995 | Emerson et al. |
| 5,416,022 A | 5/1995 | Amiot |
| 5,433,909 A | 7/1995 | Martakos et al. |
| 5,437,994 A | 8/1995 | Emerson et al. |
| 5,453,357 A | 9/1995 | Hogan |
| 5,459,069 A | 10/1995 | Palsson et al. |
| 5,460,964 A | 10/1995 | McGlave et al. |
| 5,486,389 A | 1/1996 | Gerber |
| 5,510,257 A | 4/1996 | Sirkar et al. |
| 5,541,105 A | 7/1996 | Melink et al. |
| 5,564,183 A | 10/1996 | Satou et al. |
| 5,605,822 A | 2/1997 | Emerson et al. |
| 5,622,857 A | 4/1997 | Goffe |
| 5,627,070 A | 5/1997 | Gruenberg |
| 5,631,006 A | 5/1997 | Melink et al. |
| 5,635,386 A | 6/1997 | Palsson et al. |
| 5,635,387 A | 6/1997 | Fei et al. |
| 5,646,043 A | 7/1997 | Emerson et al. |
| 5,656,421 A | 8/1997 | Gebhard et al. |
| 5,656,479 A | 8/1997 | Petitte et al. |
| 5,670,147 A | 9/1997 | Emerson et al. |
| 5,670,351 A | 9/1997 | Emerson et al. |
| 5,670,372 A | 9/1997 | Hogan |
| 5,677,136 A | 10/1997 | Simmons et al. |
| 5,677,355 A | 10/1997 | Shalaby et al. |
| 5,688,687 A | 11/1997 | Palsson et al. |

(Continued)

FOREIGN PATENT DOCUMENTS

| EP | 0220650 A2 | 5/1987 |
| JP | H02245177 A | 9/1990 |

(Continued)

OTHER PUBLICATIONS

Liu Y. et al., "Ex vivo expansion of hematopoietic stem cells derived from umbilical cord blood in rotating wall vessel", Journal of Biotechnology, 2006, vol. 124, pp. 592-601.*

(Continued)

*Primary Examiner* — Satyendra K Singh
(74) *Attorney, Agent, or Firm* — Terumo BCT, Inc. IP Law Department

(57) ABSTRACT

Described are embodiments for expanding cells in a bioreactor. In one embodiment, methods are provided that distribute cells throughout the bioreactor and attach cells to specific portions of a bioreactor to improve the expansion of the cells in the bioreactor. Embodiments may be implemented on a cell expansion system configured to load, distribute, attach and expand cells.

15 Claims, 20 Drawing Sheets

(56) References Cited

U.S. PATENT DOCUMENTS

| | | |
|---|---|---|
| 5,712,154 A | 1/1998 | Mullon et al. |
| 5,716,827 A | 2/1998 | Tsukamoto et al. |
| 5,736,396 A | 4/1998 | Bruder et al. |
| 5,750,397 A | 5/1998 | Tsukamoto et al. |
| 5,759,793 A | 6/1998 | Schwartz et al. |
| 5,763,194 A | 6/1998 | Slowiaczek et al. |
| 5,763,261 A | 6/1998 | Gruenberg |
| 5,763,266 A | 6/1998 | Palsson et al. |
| 5,766,948 A | 6/1998 | Gage et al. |
| 5,766,951 A | 6/1998 | Brown |
| 5,811,094 A | 9/1998 | Caplan et al. |
| 5,827,735 A | 10/1998 | Young et al. |
| 5,827,740 A | 10/1998 | Pittenger |
| 5,837,539 A | 11/1998 | Caplan et al. |
| 5,837,670 A | 11/1998 | Hartshorn |
| 5,843,780 A | 12/1998 | Thomson |
| 5,849,553 A | 12/1998 | Anderson et al. |
| 5,851,832 A | 12/1998 | Weiss et al. |
| 5,874,301 A | 2/1999 | Keller et al. |
| 5,882,918 A | 3/1999 | Goffe |
| 5,888,807 A | 3/1999 | Palsson et al. |
| 5,898,040 A | 4/1999 | Shalaby et al. |
| 5,908,782 A | 6/1999 | Marshak et al. |
| 5,914,268 A | 6/1999 | Keller et al. |
| 5,958,763 A | 9/1999 | Goffe |
| 5,968,829 A | 10/1999 | Carpenter |
| 5,981,211 A | 11/1999 | Hu et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,015,554 A | 1/2000 | Galy |
| 6,037,174 A | 3/2000 | Smith et al. |
| 6,040,180 A | 3/2000 | Johe |
| 6,048,721 A | 4/2000 | Armstrong et al. |
| 6,080,581 A | 6/2000 | Anderson et al. |
| 6,096,532 A | 8/2000 | Armstrong et al. |
| 6,110,739 A | 8/2000 | Keller et al. |
| 6,190,910 B1 | 2/2001 | Kusakabe et al. |
| 6,197,575 B1 | 3/2001 | Griffith et al. |
| 6,200,806 B1 | 3/2001 | Thomson |
| 6,224,860 B1 | 5/2001 | Brown |
| 6,228,635 B1 | 5/2001 | Armstrong et al. |
| 6,238,908 B1 | 5/2001 | Armstrong et al. |
| 6,306,169 B1 | 10/2001 | Lee et al. |
| 6,326,198 B1 | 12/2001 | Emerson et al. |
| 6,372,210 B2 | 4/2002 | Brown |
| 6,432,711 B1 | 8/2002 | Dinsmore et al. |
| 6,436,701 B1 | 8/2002 | Evans et al. |
| 6,500,668 B2 | 12/2002 | Samarut et al. |
| 6,566,126 B2 | 5/2003 | Cadwell |
| 6,582,955 B2 | 6/2003 | Martinez et al. |
| 6,616,912 B2 | 9/2003 | Eddleman et al. |
| 6,617,159 B1 | 9/2003 | Cancedda et al. |
| 6,617,161 B2 | 9/2003 | Luyten et al. |
| 6,642,019 B1 | 11/2003 | Anderson et al. |
| 6,667,034 B2 | 12/2003 | Palsson et al. |
| 6,680,166 B1 | 1/2004 | Mullon et al. |
| 6,703,279 B2 | 3/2004 | Lee |
| 6,835,566 B2 | 12/2004 | Smith et al. |
| 6,844,187 B1 | 1/2005 | Wechsler et al. |
| 6,875,607 B1 | 4/2005 | Reubinoff et al. |
| 6,911,201 B1 | 6/2005 | Merchav et al. |
| 6,933,144 B2 | 8/2005 | Cadwell |
| 6,943,008 B1 | 9/2005 | Ma |
| 6,969,308 B2 | 11/2005 | Doi et al. |
| 6,979,308 B1 | 12/2005 | McDonald et al. |
| 7,015,037 B1 | 3/2006 | Furcht et al. |
| 7,029,913 B2 | 4/2006 | Thomson |
| 7,033,823 B2 | 4/2006 | Chang |
| 7,037,721 B1 | 5/2006 | Wille, Jr. |
| 7,041,493 B2 | 5/2006 | Rao |
| 7,109,032 B2 | 9/2006 | Cancedda et al. |
| 7,112,437 B2 | 9/2006 | Pera |
| 7,112,441 B2 | 9/2006 | Uemura et al. |
| 7,145,057 B2 | 12/2006 | Van de Lavoir et al. |
| 7,153,684 B1 | 12/2006 | Hogan |
| 7,169,610 B2 | 1/2007 | Brown |
| 7,172,696 B1 | 2/2007 | Martinez et al. |
| 7,270,996 B2 | 9/2007 | Cannon et al. |
| 7,294,508 B2 | 11/2007 | Parikh et al. |
| 7,531,351 B2 | 5/2009 | Marx et al. |
| 7,534,609 B2 | 5/2009 | Merchav et al. |
| 7,682,822 B2 | 3/2010 | Noll et al. |
| 7,718,430 B2 | 5/2010 | Antwiler |
| 7,838,289 B2 | 11/2010 | Furcht et al. |
| 8,309,347 B2 | 11/2012 | Antwiler |
| 8,399,245 B2 | 3/2013 | Leuthaeuser et al. |
| 8,785,181 B2 | 7/2014 | Antwiler |
| 8,895,291 B2 * | 11/2014 | Dilorenzo ............. C12M 23/42 435/283.1 |
| 9,057,045 B2 * | 6/2015 | Gibbons ................ C12M 23/42 |
| 9,175,259 B2 * | 11/2015 | Nankervis ............. C12M 41/44 |
| 2001/0044413 A1 | 11/2001 | Pierce et al. |
| 2002/0164794 A1 | 11/2002 | Wernet |
| 2003/0059414 A1 | 3/2003 | Ho et al. |
| 2003/0181269 A1 | 9/2003 | Griffin |
| 2003/0224510 A1 | 12/2003 | Yamaguchi et al. |
| 2004/0027914 A1 | 2/2004 | Vrane |
| 2005/0003530 A1 | 1/2005 | Gerlach |
| 2005/0032218 A1 | 2/2005 | Gerlach |
| 2005/0153442 A1 | 7/2005 | Katz et al. |
| 2006/0019388 A1 | 1/2006 | Hutmacher et al. |
| 2006/0147246 A1 | 7/2006 | Richards |
| 2006/0205071 A1 | 9/2006 | Hasson et al. |
| 2006/0233834 A1 | 10/2006 | Guehenneux et al. |
| 2007/0122904 A1 | 5/2007 | Nordon |
| 2007/0160583 A1 | 7/2007 | Lange et al. |
| 2007/0231305 A1 | 10/2007 | Noll et al. |
| 2007/0298497 A1 | 12/2007 | Antwiler |
| 2008/0206733 A1 | 8/2008 | Tanaka et al. |
| 2008/0213894 A1 | 9/2008 | Antwiler |
| 2008/0220522 A1 | 9/2008 | Antwiler |
| 2008/0220523 A1 * | 9/2008 | Antwiler ................ C12M 25/10 435/394 |
| 2008/0227190 A1 | 9/2008 | Antwiler |
| 2008/0248572 A1 | 10/2008 | Antwiler |
| 2008/0254533 A1 | 10/2008 | Antwiler |
| 2009/0191631 A1 | 7/2009 | Bornemann |
| 2009/0196901 A1 | 8/2009 | Guilak et al. |
| 2010/0042260 A1 | 2/2010 | Antwiler |
| 2010/0105138 A1 | 4/2010 | Dodd et al. |
| 2010/0144037 A1 | 6/2010 | Antwiler |
| 2010/0209403 A1 | 8/2010 | Meiron et al. |
| 2010/0233130 A1 | 9/2010 | Meretzki |
| 2010/0267134 A1 | 10/2010 | Pera et al. |
| 2011/0159584 A1 * | 6/2011 | Gibbons ................ C12M 23/42 435/325 |
| 2012/0308531 A1 | 12/2012 | Pinxteren et al. |
| 2017/0107488 A1 | 4/2017 | Petcavich |

FOREIGN PATENT DOCUMENTS

| | | |
|---|---|---|
| JP | 2003510068 A | 3/2003 |
| JP | 2005278564 A | 10/2005 |
| JP | 2007000038 A | 1/2007 |
| JP | 2007097407 A | 4/2007 |
| WO | 86/02379 A1 | 4/1986 |
| WO | 88/01643 A1 | 3/1988 |
| WO | 90/02171 A1 | 3/1990 |
| WO | 91/07485 A1 | 5/1991 |
| WO | 91/18972 A1 | 12/1991 |
| WO | 92/10564 A1 | 6/1992 |
| WO | 95/04813 A1 | 2/1995 |
| WO | 95/13088 A1 | 5/1995 |
| WO | 95/21911 A1 | 8/1995 |
| WO | 97/16527 A1 | 5/1997 |
| WO | 98/50526 A1 | 11/1998 |
| WO | 98/53046 A1 | 11/1998 |
| WO | 99/01159 A1 | 1/1999 |
| WO | 00/75275 A2 | 12/2000 |
| WO | 01/23520 A1 | 4/2001 |
| WO | 02/28996 A1 | 4/2002 |

(56) References Cited

FOREIGN PATENT DOCUMENTS

| WO | 03/105663 | A2 | 12/2003 |
|---|---|---|---|
| WO | 2004/090112 | A2 | 10/2004 |
| WO | 2005087915 | A2 | 9/2005 |
| WO | 07/012144 | A1 | 2/2007 |
| WO | 2007/136821 | A1 | 11/2007 |
| WO | 2007/139742 | A1 | 12/2007 |
| WO | 2007/139746 | A1 | 12/2007 |
| WO | 2007/139747 | A1 | 12/2007 |
| WO | 2007/139748 | A2 | 12/2007 |
| WO | 2008/109674 | A2 | 9/2008 |
| WO | 2009/034186 | A2 | 3/2009 |
| WO | 10/034468 | A1 | 4/2010 |
| WO | 10/149597 | A2 | 12/2010 |
| WO | 2017/066663 | A1 | 4/2017 |

OTHER PUBLICATIONS

Nguyen K. Automated expansion of human mesenchymal stem cells from precultured cells using the Quantum cell expansion system, a technical white paper, published on the web (at—https://www.terumobct.com/location/latin . . ./306620113C-web.pdf) on Jul. 11, 2011, pp. 1-12.*

Chang et al., "Membrane Bioreactors: Present and Prospects", Advances in Biochemical Engineering, 1991, pp. 27-64, vol. 44.

Chang, Ho Nam, "Membrane Bioreactors: Engineering Aspects", Biotech. Adv., 1987, pp. 129-145, vol. 5.

Edgington, Stephen M., "New Horizons for Stem-Cell Bioreactors", Biotechnology, Oct. 1992, pp. 1099-1106, vol. 10.

Gastens et al., "Good Manufacturing Practice-Compliant Expansion of Marrow-Derived Stem and Progenitor Cells for Cell Therapy", Cell Transplantation, 2007, pp. 685-696, vol. 16.

Gramer et al., "Screening Tool for Hollow-Fiber Bioreactor Process Development", Biotechnol. Prog., 1998, pp. 203-209, vol. 14.

Hirschel et al., "An Automated Hollow Fiber System for the Large Scale Manufacture of Mammalian Cell Secreted Product", Large Scale Cell Culture Technology, ed. Bjorn K. Lydersen, 1987, pp. 113-144, Hanser Publishers.

Infanger et al., "Simulated weightlessness changes the cytoskeleton and extracellular matrix proteins in papillary thyroid carcinoma cells", Cell and Tissue Research, 2006, 324(2): 267-277.

International Search Report and Written Opinion, PCT/US2014/065829, dated Jan. 21, 2015.

Jones et al., "Genetic stability of bone marrow-derived human mesenchymal stromal cells in the Quantum System", Cytotherapy, 2013; 15: 1323-1339.

Nankervis et al., "Shear Stress Conditions in the Quantum Cell Expansion System", Poster Session—TERMIS AM Annual Conference 2013, Nov. 12, 2013.

Nielsen, Lars Keld, "Bioreactors for Hematopoietic Cell Culture", Annu. Rev. Biomed. Eng., 1999, vol. 1, pp. 129-152.

Office Action, U.S. Appl. No. 14/542,276, dated Jun. 17, 2016.

Pörtner et al., "An Overview on Bioreactor Design, Prototyping and Process Control for Reproducible Three-Dimensional Tissue Culture", Drug Testing in Vitro: Breakthroughs and Trends in Cell Culture Technology, ed. Uwe Marx and Volker Sandig, 2007, Wiley-VCH, pp. 53-78.

Zhao et al., "Perfusion Bioreactor System for Human Mesenchymal Stem Cell Tissue Engineering: Dynamic Cell Seeding and Construct Development", Biotechnology and Bioengineering, Aug. 20, 2005, vol. 91, No. 4, pp. 482-493.

Notice of Allowance, U.S. Appl. No. 14/542,276, dated Dec. 12, 2016.

First Office Action, Chinese Patent Application No. 201480065645.1, dated Jun. 2, 2017 (English language translation included).

First Office Action, Chinese Patent Application No. 201480065648.5, dated Jun. 2, 2017 English language translation included).

Invitation pursuant to Article 94(3) and Rule 71 (1) EPC, European Patent Application No. 14806151.8, dated Mar. 14, 2017.

Invitation pursuant to Article 94(3) and Rule 71 (1) EPC, European Patent Application No. 14806152.6, dated Mar. 15, 2017.

Antwiler et al., 'Quantum® Cell Expansion System: Process Optimization for Expansion of Bone Marrow-Derived Mesenchymal Stem Cells (MSCs), International Society for Cell Therapy (ISCT), 2011.

Office Action, Japanese Patent Application No. 2016-530921, dated Aug. 28, 2018 (English language translation included).

Office Action, Japanese Patent Application No. 2016-531019, dated Oct. 23, 2018 (English language translation included).

Office Action, Japanese Patent Application No. 2016-530921, dated Feb. 26, 2019 (English language translation included).

Office Action, Japanese Patent Application No. 2016-531019, dated May 14, 2019 (English language translation included).

Campagnoli Cesare, et al.: "Identification of mesenchymal stem/progenitor cells in human first-trimester fetal blood, liver, and bone marrow," Blood, American Society of Hematology, US, vol. 98, No. 8, Oct. 15, 2001 (Oct. 15, 2001), pp. 2396-2402.

Colter, David Co., et al., "Rapid expansion of recycling stem cells in cultures of plastic-adherent cells from human bone marrow," PNAS, Mar. 28, 2000, col. 97, No. 7, pp. 3213-3218.

Deans, Robert J., et al., "Mesenchymal stem cells: Biology and potential clinical uses," Experimental Hematology, 28 (2000), pp. 875-884.

De Kreuk, Arne M., et al., "A Single-Step Colony-Forming Unit Assay for Unseparated Mobilised Peripheral Blood, Cord Blood, and Bone Marrow," Journal of Hematotherapy & Stem Cell Research, Mary Ann Liebert, Inc., 2001, vol. 10, pp. 795-806.

Deppisch, Reinhold, et al., "Microdomain structure of plumerica surfaces—Potential for improving blood treatment procedures," Nephrol Dial Transplant, 1998, vol. 13, pp. 1354-1359.

Humes, HD, et al., "The future of hemodialysis membranes," Kidney International, 2006, col. 69, pp. 1115-1119.

Javazon, Elisabeth H., et al., "Rat Marrow Stromal Cells are More Sensitive to Plating Density and Expand More Rapidly from Single-Cell-Derived Colonies than Human Marrow Stromal Cells," Stem Cells, 2001, vol. 19, pp. 219-225.

Lin, Wen-Ching, et al., "Blood compatibility of thermoplastic polyurethane membrane immobilized with water soluble chitosan/dextran sulfate," Colloids and Surfaces B: Biointerfaces, 2005, col. 44, pp. 82-92.

Martin, Ivan, et al., "Selective differentiation of mammalian bone marrow stromal cells cultured on three-dimensional polymer foams," Engineering Skeletal Tissues from Bone Marrow, John Wiley & Sons, Inc., 2001, pp. 229-235.

Mesquita, Fernanda C. Paccola, et al., "Laminin as a Potent Substrate for Large-Scale Expansion of Human Induced Pluripotent Stem Cells in a Closed Cell Expansion System," Hindawi, Stem Cells International, vol. 2019, Article ID 9704945, Jan. 22, 2019, pp. 1-9.

Sekiya, Ichiro, et al., "Expansion of Human Adult Stem Cells from Bone Marrow Stroma: Conditions that Maximize the Yields of Early Progenitors and Evaluate Their Quality," Stem Cells, 2002, vol. 20, pp. 530-541.

Sheu, Jonathan, et al., "Large-scale production of lentiviral vector in a closed system hollow fiber bioreactor," Nature, Molecular Therapy—Mehtods & Clinical Development, 2, Article number: 15020 (2015), doi:10.1038/mtm.2015.20, Jun. 17, 2015, <http://www.nature.com/articels/mtm201520>, pp. 1-18.

Sotiropoulou, Panagiota A., et al., "Characterization of the Optimal Culture Conditions for Clinical Scale Production of Human Mesenchymal Stem Cells," Stem Cells, 2006, vol. 24, pp. 462-471.

Tsai, Ming-Song, et al., "Isolation of human mulipotent mesenchymal stem cells from second-trimester amniotic fluid using a novel two-stage culture protocol," Human Reproduction, 2004, vol. 19, No. 6, pp. 1450-1456.

* cited by examiner

EXPANDING CELLS IN A BIOREACTOR

CROSS-REFERENCE TO RELATED PATENT APPLICATION(S)

This application claims priority to U.S. Provisional Patent Application No. 61/905,182 filed Nov. 16, 2013, entitled METHOD OF LOADING AND DISTRIBUTING CELLS IN A BIOREACTOR OF A CELL EXPANSION SYSTEM, which is hereby incorporated by reference in its entirety as if set forth herein in full.

BACKGROUND

The potential use of stem cells in a variety of treatments and therapies has achieved particular attention. Cell expansion systems can be used to expand, e.g., grow, stem cells, as well as other types of cells, such as bone marrow cells. Stem cells which are expanded from donor cells can be used to repair or replace damaged or defective tissues and have broad clinical applications for a wide range of diseases. Recent advances in the regenerative medicine field demonstrates that stem cells have properties such as proliferation and self-renewal capacity, maintenance of the unspecialized state, and the ability to differentiate into specialized cells under particular conditions.

Cell expansion systems include one or more compartments for expanding the cells, such as a cell growth chamber, also referred to herein as a "bioreactor." In order to expand cells, an initial volume of cells is typically loaded into, and distributed within, the bioreactor. Accordingly, there is a need for a method of loading and distributing cells in a bioreactor associated with a cell expansion system. The present disclosure addresses this and other needs.

Embodiments of the present invention have been made in light of these and other considerations. However, the relatively specific problems discussed above do not limit the applicability of the embodiments of the present invention to solving other problems.

SUMMARY

The summary is provided to introduce aspects of some embodiments of the present invention in a simplified form, and is not intended to identify key or essential elements of the claimed invention, nor is it intended to limit the scope of the claims.

It is to be understood that the present invention may include a variety of different versions or embodiments, and this Summary is not meant to be limiting or all-inclusive. This Summary provides some general descriptions of features that may be included in embodiments, and also include some more specific descriptions of other features that may be included in other embodiments.

One or more embodiments are generally directed to a method and system for loading and distributing cells in a bioreactor of a cell expansion system. Accordingly, embodiments include methods that may provide for adding a plurality of cells to a fluid circulating at a first rate within a bioreactor of the cell expansion system. In embodiments, the bioreactor may include a hollow fiber membrane with a plurality of individual hollow fibers through which the cells and other fluids are circulated. Initially, fluid is circulated through the hollow fiber membrane of the bioreactor and cells are added to the circulating fluid. The fluid is circulated at a first predetermined circulation rate. During circulation, the bioreactor may be in a horizontal position. After the cells are loaded by being added to the circulation fluid, the cells may be allowed to circulate and distribute evenly throughout the system, with cells flowing into and out of the hollow fibers of the hollow fiber membrane. The circulation may then be stopped. The cells are then allowed to settle, under the influence of gravity, and attached to a first portion of the hollow fibers in the bioreactor. In embodiments, the cells may be allowed to settle for a first predetermined period of time. In some embodiments, the predetermined period of time may be selected to allow the cells also to attach to the first portion of the hollow fibers.

After the first predetermined period of time, the bioreactor is rotated 180 degrees. After rotation of the bioreactor, cells within the bioreactor are allowed to settle again. Cells may then settle on an opposing portion of the hollow fibers for a second predetermined period of time that may be selected to also allow the cells to attach to the opposing portion. After the second predetermined period of time, the bioreactor is rotated back to its original horizontal position and the cells undergo an expansion process.

In some embodiments, the loading process includes additional steps. In some embodiments, after the bioreactor is returned to its original horizontal position, circulation is restarted. The circulation rate may be set at a lower rate than the first predetermined circulation rate. The circulation would be performed to once again distribute cells that have not attached to a surface. The circulation would continue for a third predetermined period of time to allow unattached cell to become evenly distributed throughout the system including the bioreactor. The circulation would then be stopped allowing cells in the bioreactor to settle, and in embodiments attach to portions of the hollow fibers, once again.

After a fourth predetermined period of time to allow the cells to settle again, the bioreactor is rotated 180 degrees. After rotation of the bioreactor, cells within the bioreactor are allowed to settle again. Cells may then settle on an opposing portion of the hollow fibers for a fifth predetermined period of time that may be selected to also allow the cells to attach to the opposing portion of the hollow fibers. After the fifth predetermined period of time, the bioreactor is rotated back to its original horizontal position.

The process is again repeated by circulating cells in the system to evenly distribute any unattached cells, again. However, each time circulation is restarted, it is restarted at a lower rate than the previous circulation. When the circulation is stopped, the cells are allowed to settle and attach. The bioreactor is rotated 180 degrees and the cells are allowed to settle and attach. Then the bioreactor is rotated back to its original position. These steps of circulation, settling, rotation, settling, and rotation may be repeated a predetermined number of times, after which the attached cells, which have been attached in layers, are expanded in the bioreactor.

Other embodiments are also directed to a method and system for loading and distributing cells in a bioreactor of a cell expansion system. Embodiments include methods that may provide for adding a plurality of cells to a fluid circulating at a first rate within a bioreactor of the cell expansion system. In embodiments, the bioreactor may include a hollow fiber membrane with a plurality of individual hollow fibers through which the cells and other fluids are circulated. Initially, fluid is circulated through the hollow fiber membrane of the bioreactor and cells are added to the circulating fluid. The fluid is circulated at a first predetermined circulation rate. During circulation, the bioreactor may be in a horizontal position. After the cells are loaded by being added to the circulation fluid, the cells may be allowed to circulate and distribute evenly throughout the system, with cells flowing into and out of the hollow fibers of the hollow fiber membrane. The circulation may then be stopped. The cells are then allowed to settle, under the influence of gravity, and attached to a first portion of the hollow fibers in the bioreactor. In embodiments, the cells may be allowed to settle for a first predetermined period of time. In some embodiments, the predetermined period of time may be selected to allow the cells also to attach to the first portion of the hollow fibers.

After the first predetermined period of time, the bioreactor is rotated 180 degrees. After rotation of the bioreactor, the cells undergo an expansion process. As may be appreciated, the previously attached cells may be on a top portion of the hollow fibers. As the cells are expanded, they may be subjected to gravity, which may influence cell growth toward a bottom portion of the hollow fibers.

Additional advantages of the embodiments presented herein will become readily apparent from the following discussion, particularly when taken together with the accompanying drawings.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

The principles of the present invention may be further understood by reference to the following detailed description and the embodiments depicted in the accompanying drawings. It should be understood that although specific features are shown and described below with respect to detailed embodiments, the present invention is not limited to the embodiments described below. The present disclosure is generally directed to a method for distributing a plurality of cells in a bioreactor of a cell expansion system. As described below, a method of distributing cells within a bioreactor may include loading cells into the bioreactor, rotating the bioreactor, and holding the bioreactor still at certain orientations.

Figure 1A:
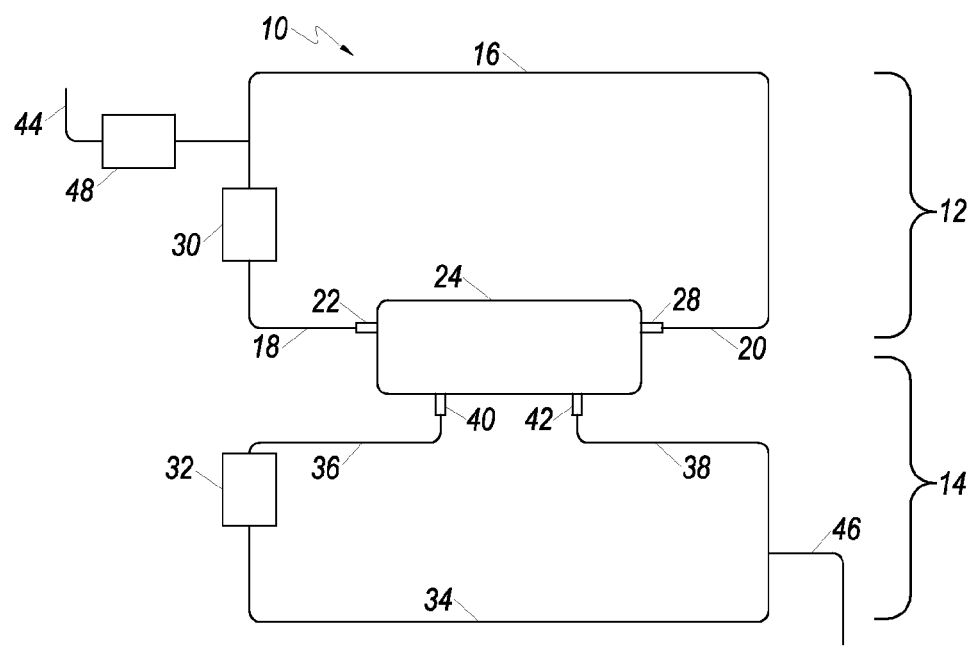
FIG. 1A depicts one embodiment of a cell expansion system (CES).

A schematic of an example cell expansion system (CES) is depicted in FIG. 1A. CES 10 includes first fluid circulation path 12 and second fluid circulation path 14. First fluid flow path 16 has at least opposing ends 18 and 20 fluidly associated with a hollow fiber cell growth chamber 24 (also referred to herein as a "bioreactor"). Specifically, opposing end 18 is fluidly associated with a first inlet 22 of cell growth chamber 24, and opposing end 20 is fluidly associated with first outlet 28 of cell growth chamber 24. Fluid in first circulation path 12 flows through the interior of hollow fibers of hollow fiber membrane disposed in cell growth chamber 24 (cell growth chambers and hollow fiber membranes are described in more detail infra). Further, first fluid flow controller 30 is operably connected to first fluid flow path 16, and controls the flow of fluid in first circulation path 12.

Second fluid circulation path 14 includes second fluid flow path 34, cell growth chamber 24, and a second fluid flow controller 32. The second fluid flow path 34 has at least opposing ends 36 and 38. Opposing ends 36 and 38 of second fluid flow path 34 are fluidly associated with inlet port 40 and outlet port 42 respectively of cell growth chamber 24. Fluid flowing through cell growth chamber 24 is in contact with the outside of hollow fiber membrane in the cell growth chamber 24. Second fluid circulation path 14 is operably connected to second fluid flow controller 32.

First and second fluid circulation paths 12 and 14 are thus separated in cell growth chamber 24 by a hollow fiber membrane. Fluid in first fluid circulation path 12 flows through the intracapillary ("IC") space of the hollow fibers in the cell growth chamber. First circulation path 12 is thus referred to as the "IC loop." Fluid in second circulation path 14 flows through the extracapillary ("EC") space in the cell growth chamber. Second fluid circulation path 14 is thus referred to as the "EC loop." Fluid in first fluid circulation path 12 can flow in either a co-current or counter-current direction with respect to flow of fluid in second fluid circulation path 14.

Fluid inlet path 44 is fluidly associated with first fluid circulation path 12. Fluid inlet path 44 allows fluid into first fluid circulation path 12, while fluid outlet path 46 allows fluid to leave CES 10. Third fluid flow controller 48 is operably associated with fluid inlet path 44. Alternatively, third fluid flow controller 48 can alternatively be associated with fluid outlet path 46.

Fluid flow controllers as used herein can be a pump, valve, clamp, or combination thereof. Multiple pumps, valves, and clamps can be arranged in any combination. In various embodiments, the fluid flow controller is or includes a peristaltic pump. In further embodiments, fluid circulation paths, inlet ports, and outlet ports can be constructed of tubing of any material.

Various components are referred to herein as "operably associated." As used herein, "operably associated" refers to components that are linked together in operable fashion, and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g. a peristaltic pump that pumps fluids through flexible tubing by compressing the exterior of the tube).

Generally, any kind of fluid, including buffers, protein containing fluid, and cell-containing fluid can flow through the various circulations paths, inlet paths, and outlet paths. As used herein, "fluid," "media," and "fluid media" are used interchangeably.

Figure 1B:
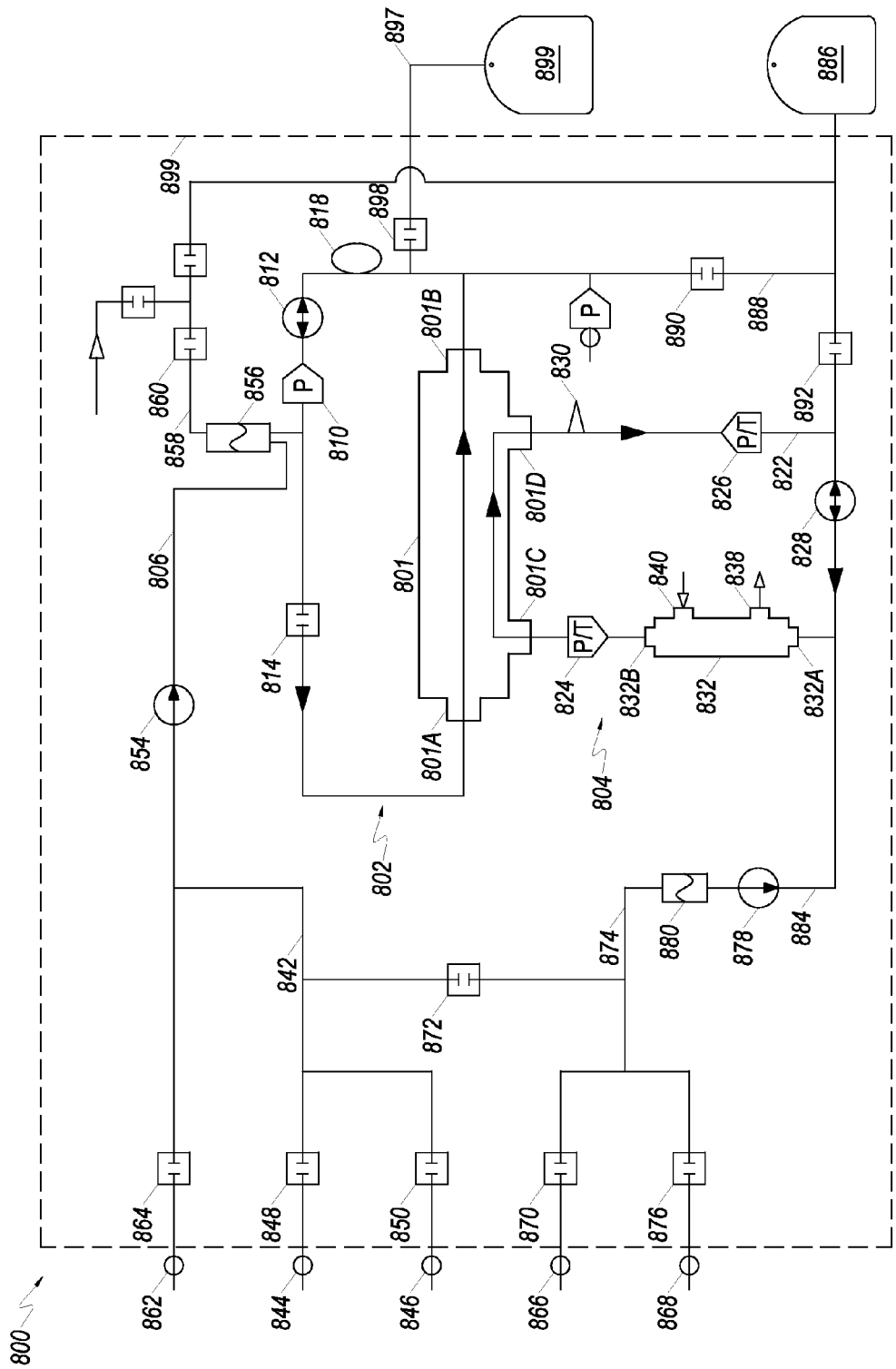
FIG. 1B depicts a second embodiment of a CES.

FIG. 1B depicts a more detailed cell expansion system 800. CES 800 includes a first fluid circulation path 802 (also referred to as the "intracapillary loop" or "IC loop") and second fluid circulation path 804 (also referred to as the "extracapillary loop" or "EC loop"). First fluid flow path 806 is fluidly associated with cell growth chamber 801 through fluid circulation path 802. Fluid flows into cell growth chamber 801 through IC inlet port 801A, through hollow fibers in cell growth chamber 801, and exits via IC outlet port 801B. Pressure sensor 810 measures the pressure of media leaving cell growth chamber 801. In addition to pressure, sensor 810 may in embodiments also be a temperature sensor that detects the media pressure and temperature during operation. Media flows through IC circulation pump 812 which can be used to control the rate of media flow, e.g., circulation rate in the IC loop. IC circulation pump 812 may pump the fluid in a first direction or second direction opposite the first direction. Exit port 801B can be used as an inlet in the reverse direction. Media entering the IC loop 802 may enter through valve 814. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the CES 800 and modifications to the schematic shown are within the scope of the one or more present embodiments.

With regard to the IC loop 802, samples of media can be obtained from sample coil 818 during operation. Media then returns to IC inlet port 801A to complete fluid circulation path 802. Cells grown/expanded in cell growth chamber 801 can be flushed out of cell growth chamber 801 into harvest bag 899 through valve 898 and line 897. Alternatively, when valve 898 is closed, the cells may be redistributed, e.g., circulated back, within chamber 801 for further growth or loading.

Fluid in second fluid circulation path 804 enters cell growth chamber 801 via EC inlet port 801C, and leaves cell growth chamber 801 via EC outlet port 801D. Media in the EC loop 804 is in contact with the outside of the hollow fibers in the cell growth chamber 801, thereby allowing diffusion of small molecules into and out of the hollow fibers that may be within chamber 801.

Pressure/temperature sensor 824 disposed in the second fluid circulation path 804 allows the pressure and temperature of media to be measured before the media enters the EC space of the cell growth chamber 801. Sensor 826 allows the pressure and temperature of media in the second fluid circulation path 804 to be measured after it leaves the cell growth chamber 801. With regard to the EC loop 804, samples of media can be obtained from sample port 830 or a sample coil during operation.

After leaving EC outlet port 801D of cell growth chamber 801, fluid in second fluid circulation path 804 passes through EC circulation pump 828 to gas transfer module 832. EC circulation pump 828 may also pump the fluid in opposing directions. Second fluid flow path 822 is fluidly associated with gas transfer module 832 via an inlet port 832A and an outlet port 832B of gas transfer module 832. In operation, fluid media flows into gas transfer module 832 via inlet port 832A, and exits gas transfer module 832 via outlet port 832B. Gas transfer module 832 adds oxygen to and removes bubbles from media in the CES 800. In various embodiments, media in second fluid circulation path 804 is in equilibrium with gas entering gas transfer module 832. The gas transfer module 832 can be any appropriately sized device known in the art and useful for oxygenation or gas transfer. Air or gas flows into gas transfer module 832 via filter 838 and out of oxygenator or gas transfer device 832 through filter 840. Filters 838 and 840 reduce or prevent contamination of oxygenator 832 and associated media. Air or gas purged from the CES 800 during portions of a priming sequence can vent to the atmosphere via the gas transfer module 832.

In the configuration depicted for CES 800, fluid media in first fluid circulation path 802 and second fluid circulation path 804 flows through cell growth chamber 801 in the same direction (a co-current configuration). The CES 800 can also be configured to flow in a counter-current conformation.

In accordance with at least one embodiment, media, including cells (from a source such as a cell container, e.g. a bag) can be attached at attachment point 862, and fluid media from a media source can be attached at attachment point 846. The cells and media can be introduced into first fluid circulation path 802 via first fluid flow path 806. Attachment point 862 is fluidly associated with the first fluid flow path 806 via valve 864, and attachment point 846 is fluidly associated with the first fluid flow path 806 via valve 850. A reagent source may be fluidly connected to point 844 and be associated with fluid inlet path 842 via valve 848, or second fluid inlet path 874 via valves 848 and 872.

Air removal chamber (ARC) 856 is fluidly associated with first circulation path 802. The air removal chamber 856 may include one or more sensors including an upper sensor and lower sensor to detect air, a lack of fluid, and/or a gas/fluid interface, e.g., an air/fluid interface, at certain measuring positions within the air removal chamber 856. For example, ultrasonic sensors may be used near the bottom and/or near the top of the air removal chamber 856 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 800 during portions of the priming sequence or other protocols can vent to the atmosphere out air valve 860 via line 858 that is fluidly associated with air removal chamber 856.

An EC media source may be attached to EC media attachment point 868 and a wash solution source may be attached to wash solution attachment point 866, to add EC media and/or wash solution to either the first or second fluid flow path. Attachment point 866 may be fluidly associated with valve 870 that is fluidly associated with first fluid circulation path 802 via valve 872 and first fluid inlet path 842. Alternatively, attachment point 866 can be fluidly associated with second fluid circulation path 804 via second fluid inlet path 874 and EC inlet path 884 by opening valve 870 and closing valve 872. Likewise, attachment point 868 is fluidly associated with valve 876 that may be fluidly associated with first fluid circulation path 802 via first fluid inlet path 842 and valve 872. Alternatively, fluid container 868 may be fluidly associated with second fluid inlet path 874 by opening valve 876 and closing valve distribution 872.

In the IC loop 802, fluid may be initially advanced by the IC inlet pump 854. In the EC loop 804, fluid is initially advanced by the EC inlet pump 878. An air detector 880, such as an ultrasonic sensor, may also be associated with the EC inlet path 884.

In at least one embodiment, first and second fluid circulation paths 802 and 804 are connected to waste line 888. When valve 890 is opened, IC media can flow through waste line 888 and to waste bag 886. Likewise, when valve 892 is opened, EC media can flow to waste bag 886.

After cells have been grown in cell growth chamber 801, they may be harvested via cell harvest path 897. Here, cells from cell growth chamber 801 can be harvested by pumping the IC media containing the cells through cell harvest path 897, with valve 898 open, into cell harvest bag 899.

Figure 1C:
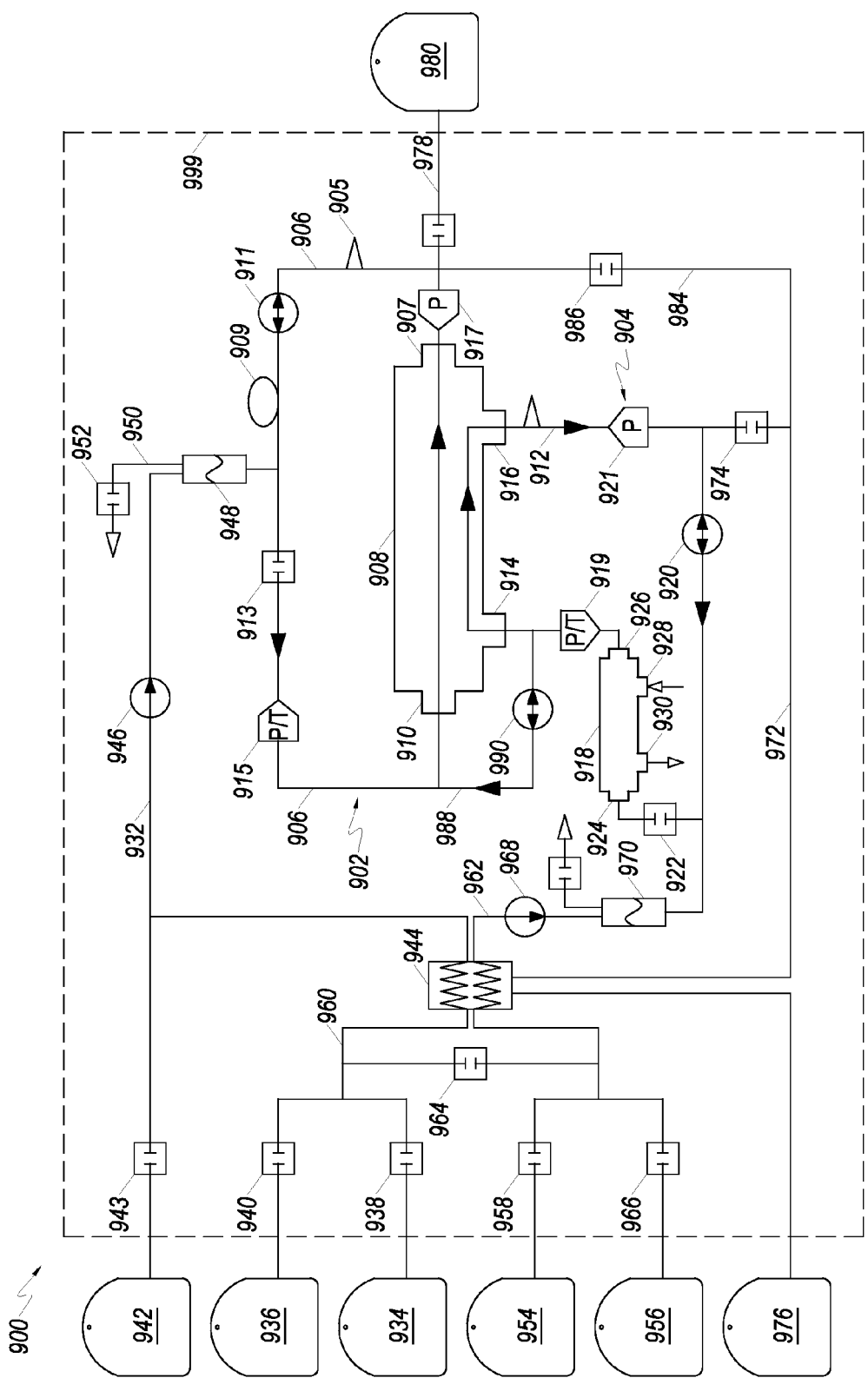
FIG. 1C depicts a third embodiment of a CES.

Various components of the CES 800 can be contained or housed within a machine or housing 899, such as cell expansion machine, wherein the machine maintains cells and media at a predetermined temperature. It is further noted that in embodiments, components of CES 800 may be combined with other CES's such as CES 10 (FIG. 1A) or CES 900 (FIG. 1C). In other embodiments, a CES may include fewer components than shown in FIG. 1A-C and still be within the scope of the present disclosure.

FIG. 1C depicts another embodiment of a CES. CES 900 includes first fluid circulation path 902 (also referred to as the "intracapillary (IC) loop") and second fluid circulation path 904 (also referred to as the "extracapillary loop" or "EC loop").

First fluid flow path 906 is fluidly associated with cell growth chamber 908 through first fluid circulation path 902. Fluid flows into cell growth chamber 908 through inlet port 910, through hollow fibers in cell growth chamber 908, and exits via outlet port 907. Pressure gauge 917 measures the pressure of media leaving cell growth chamber 908. Media flows through valve 913 and pump 911, which can be used to control the rate of media flow. Samples of media can be obtained from sample port 905 or sample coil 909 during operation. Pressure/temperature gauge 915 disposed in first fluid circulation path 902 allows detection of media pressure and temperature during operation. Media then returns to inlet port 910 to complete fluid circulation path 902. Cells expanded in cell growth chamber 908 can be flushed out of cell growth chamber 908 or redistributed within hollow fibers for further growth.

Second fluid circulation path 904 includes second fluid flow path 912 that is fluidly associated with cell growth chamber 908 in a loop. Fluid in second fluid circulation path 904 enters cell growth chamber 908 via inlet port 914, and leaves cell growth chamber 908 via outlet port 916. Media is in contact with the outside of the hollow fibers in the cell growth chamber 908, allowing diffusion of small molecules into and out of the hollow fibers.

Pressure/temperature gauge 919 disposed in the second circulation path 904 allows the pressure and temperature of media to be measured before the media enters the EC space of the cell growth chamber 908. Pressure gauge 921 allows the pressure of media in the second circulation path 904 to be measured after it leases leaves the cell growth chamber 908.

After leaving outlet port 916 of cell growth chamber 908, fluid in second fluid circulation path 904 passes through pump 920 and valve 922 to oxygenator 918. Second fluid flow path 912 is fluidly associated with oxygenator 918 via oxygenator inlet port 924 and oxygenator outlet port 926. In operation, fluid media flows into oxygenator 918 via oxygenator inlet port 924, and exits oxygenator 918 via oxygenator outlet port 926.

Oxygenator 918 adds oxygen to media in the CES 900. In various embodiments, media in second fluid circulation path 904 is in equilibrium with gas entering oxygenator 918. The oxygenator can be any oxygenator known in the art. Gas flows into oxygenator 918 via filter 928 and out of oxygenator 918 through filter 930. Filters 928 and 930 reduce or prevent contamination of oxygenator 918 and associated media.

In the configuration depicted for CES 900, fluid media in first circulation path 902 and second circulation path 904 flow through cell growth chamber 908 in the same direction (a co-current configuration). Those of skill in the art will recognize that CES 900 can also be configured in a counter-current conformation. Those of skill in the art will recognize that the respective inlet and outlet ports can be disposed in the cell growth chamber 908 at any location.

Cells and fluid media can be introduced to fluid circulation path 902 via first fluid inlet path 932. Fluid container 934 and fluid container 936 are fluidly associated with first fluid inlet path 932 via valves 938 and 940 respectively. Likewise, cell container 942 is fluidly associated with first fluid circulation path 902 via valve 943. Cells and fluid may in some embodiments proceed through heat exchanger 944, pump 946, and into drip chamber 948. In embodiments where cells from container 942 are passed through heat exchanger 944, an additional line (not shown) would be used to connect container 942 to heat exchanger 944. Drip chamber 948 is fluidly associated with first circulation path 902. Overflow from drip chamber 948 can flow out of drip chamber 948 from overflow line 950 via valve 952.

Additional fluid can be added to first or second fluid circulation paths 902 and 904 from fluid container 954 and fluid container 956. Fluid container 954 is fluidly associated with valve 958 which is fluidly associated with first fluid circulation path 902 via valve 964, patt 960, and path 932. Alternatively, fluid container 954 is fluidly associated with second fluid inlet path 962. Likewise, fluid container 956 is fluidly associated with valve 966, which is fluidly associated with first fluid circulation path 902 via first fluid inlet path 960. Alternatively, fluid container 956 is fluidly associated with second fluid inlet path 962.

Second fluid inlet path 962 is configured to allow fluid to flow through heat exchanger 944, pump 968, before entering drip chamber 970. Second fluid inlet path 962 continues to second fluid circulation path 904. Overflow fluid can flow out via overflow line 972 through valve 974 to waste container 976.

Cells can be harvested via cell harvest path 978. Cells from cell growth chamber 908 can be harvested by pumping media containing the cells through cell harvest path 978 to cell harvest bag 980, when valve 982 is opened.

First and second fluid circulation paths 902 and 904 are connected by connector path 984. When valve 986 is opened, media can flow through connector path 984 between first and second circulation paths 902 and 904. Likewise, pump 990 can pump media through another connector path 988 between first and second fluid circulation paths 902 and 904.

Various components of the CES 900 can be contained within incubator 999. Incubator 999 maintains cells and media at a constant temperature.

As will be recognized by those of skill in the art, any number of fluid containers (e.g. media bags) can be fluidly associated with the CES 900 in any combination. It will further be noted that the location of the drip chamber 948, or sensors independent of the drip chamber 948, can be at any location in the CES 900 before inlet port 910.

CES's 800 and 900 can include additional components. For example, one or more pump loops (not shown) can be added at the location of peristaltic pumps on a CES. The pump loops may be made of polyurethane (PU) (available as Tygothane C-210A)). Alternatively, a cassette for organizing the tubing lines and which may also contain tubing loops for the peristaltic pumps may also be included as part of the disposable.

A detachable flow circuit (also referred to herein as a "detachable circulation module") may also be provided in some embodiments. The detachable flow circuit may be a portion of a cell expansion module configured to attach to a more permanent fixed portion of the CES. Generally, the fixed portions of the CES include peristaltic pumps. In various embodiments, the fixed portions of the CES can include valves and/or clamps.

The detachable flow circuit can include a first fluid flow path having at least two ends. The first end is configured to be fluidly associated with a first end of a cell growth chamber, and a second end of the first fluid flow path configured to fluidly associated with a second end of the cell growth chamber.

Likewise, the detachable flow circuit can include a second fluid flow path having at least two ends. Portions of the detachable flow circuit can be configured to be fluidly associated with an oxygenator and/or bioreactor. The detachable flow circuit can include a second fluid flow path that may be configured to fluidly associate with the oxygenator and cell growth chamber.

In various embodiments, the detachable flow circuit may be detachably and disposably mounted to a fluid flow controller. The detachable flow circuit can include detachable fluid conduits (e.g. flexible tubing) that connects portions of the CES.

In further embodiments, the detachable flow circuit can include a cell growth chamber, oxygenator, as well as bags for containing media and cells. In various embodiments, the components can be connected together, or separate. Alternatively, detachable flow circuit can include one or more portions configured to attach to fluid flow controllers, such as valves, pumps, and combinations thereof. In variations where peristaltic pumps are used, the detachable circuit module can include a peristaltic loop configured to fit around a peristaltic portion of the tubing. In various embodiments, the peristaltic loop can be configured to be fluidly associated with the circulations paths, inlet paths, and outlet paths. The detachable flow circuit can be combined in a kit with instructions for its assembly or attachments to fluid flow controllers, such as pumps and valves.

Embodiments provide for using a number of different methods to introduce cells into bioreactors of CES. As described in greater detail below, embodiments include methods and systems that distribute cells in the bioreactor to promote consistent expansion of cells.

According to embodiments, cells can be grown ("expanded") in either the IC loop or the EC loop. Adherent and non-adherent suspension cells can be expanded. In one embodiment, the lumen of the cell growth chamber fibers can be coated with fibronectin. Divalent cation-free (e.g. calcium and magnesium-free) PBS is added to a CES system. After adherent cells are introduced into a cell growth chamber, e.g., chamber 24, 801, or 908 they are incubated for a sufficient time to adhere to the hollow fibers. IC and EC media are circulated to ensure sufficient nutrients are supplied to the cells.

The flow rate of the IC loop and EC loop can be adjusted to a specific value. In various embodiments, the flow rate of the IC loop and EC loops can be, independently set to, about 2, about 4, about 6, about 8, about 10, about 15, about 20, about 25, about 30, about 35, about 40, about 45, about 50, about 60, about 70, about 80, about 90, about 100, about 200, about 300, about 400 or even about 500 mL/minute. In various embodiments, the flow rates for the IC circuit loop may be set from about 10 to about 20 mL/minute, and the flow rate of the EC circuit loop may be set from 20 to about 30 mL per minute (allowing media to flow through an oxygenator and re-establish oxygen levels). Additional media may be pumped into the CES at a lower flow rate (e.g. 0.1 mL per minute in some embodiments) to replace media that evaporates through a gas exchange module(s) such as gas exchange/oxygenators 832 and 918. In various embodiments, the EC loop removes cellular waste, and the IC loop includes growth factors in the media.

CES's may provide a great deal of flexibility in varying growth conditions and criteria. Cells can be kept in suspension in the IC loop by circulating media continuously. Alternatively, media circulation can be stopped, causing cells to settle. Fresh media can be added to the IC loop by ultrafiltration to accommodate excess volume without removing cells. EC media circulation allows for exchange of gas, nutrients, waste products, and addition of new media without removing cells.

Expanded cells can include adherent cells, non-adherent cells, or a co-culture of any combination of cells in the art. Some non-limiting examples of cells that maybe grown in a embodiments of a CES, include, without limitation, stem cells (e.g., mesenchymal, hematopoietic, etc.), fibroblasts, keratinocytes, progenitor cells, other fully differentiated cells and combinations thereof.

In embodiments, to harvest adherent cells, the IC and EC media may be replaced with media that is free of divalent cations (e.g. divalent cation-free PBS). In one embodiment, trypsin may be loaded into a first circulation path, and allowed to incubate with adherent cells for a period of time (in some embodiments about 5 to about 10 minutes). The trypsin may then be flushed from the system. A shearing force may be applied to the cells by increasing the flow rate through cell growth chamber, and adherent cells that are released from the cell growth chamber may be pumped to a cell harvest bag.

When non-adherent cells are expanded, the cells can be flushed from the circulating IC circuit. Adherent cells remain in the cell growth chamber, while non-adherent cells are removed.

The CES can be used to perform a variety of cell expansion methods. In one embodiment, a seeded population of cells can be expanded. Cells are introduced, or seeded, into the CES. In certain circumstances, the lumen of the hollow fibers can be conditioned to allow cell adhesion. Cells are then added to the cell growth chamber, and adherent cells adhere to the hollow fibers, while non-adherent cells (e.g. hematopoietic stem cells, or HSCs) do not adhere. The non-adherent cells can be flushed from the system. After incubation for a period of time, the adherent cells can be released and harvested.

The cell growth chamber of the cell expansion system in embodiments includes a hollow fiber membrane comprised of a plurality of semi-permeable hollow fibers separating first and second fluid circulation paths.

Figure 1D:
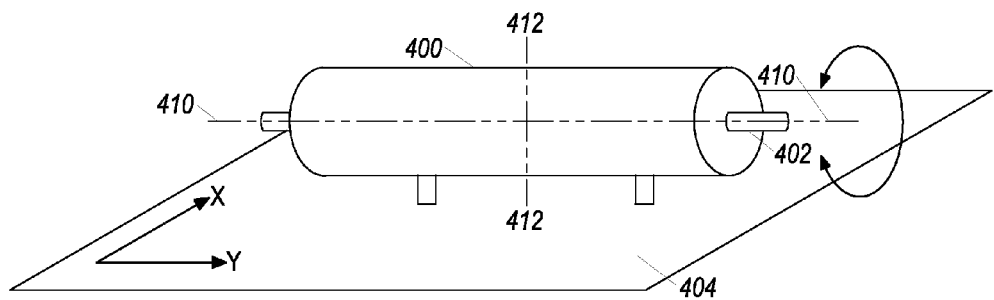
FIG. 1D depicts an embodiment of a rocking device for moving a cell growth chamber rotationally or laterally during operation of the CES.

The CES can include a device configured to move or "rock" the cell growth chamber relative to other components of the cell expansion system by attaching it to a rotational and/or lateral rocking device. FIG. 1D shows one such device, in which a bioreactor 400 is rotationally connected to two rotational rocking components, and a lateral rocking component.

A first rotational rocking device component 402 rotates the bioreactor 400 around central axis 410 of the bioreactor. Bioreactor 400 is also connected to lateral rocking device 404. Rotational rocking device component 402 is rotationally associated to bioreactor 400. The rotational rocking device 402 then rotates bioreactor 400 around central axis 410 of the bioreactor. Rotation can occur in a clockwise or counter-clockwise direction. Bioreactor 400 can be rotated continuously in a single direction around central axis 410 in a clockwise or counterclockwise direction. Alternatively, bioreactor 400 can rotate in alternating fashion, first clockwise, then counterclockwise around central axis 410.

The CES can also include a second rotational rocking component that rotates bioreactor 400 around rotational axis 412. Rotational axis 412 passes through the center of point of bioreactor 400 and is normal to central axis 410. Bioreactor 400 can be rotated continuously in a single direction around rotational axis 412 in a clockwise or counterclockwise direction. Alternatively, bioreactor 400 can be rotated around rotational axis 412 in an alternating fashion, first clockwise, then counterclockwise. In various embodiments, bioreactor 400 can also be rotated around rotational axis 412 and positioned in a horizontal or vertical orientation relative to gravity.

Lateral rocking component 404 is laterally associated with bioreactor 400. The plane of lateral rocking component 404 moves laterally in the −x and −y directions. The settling of cells in the bioreactor 400 is thereby reduced with the movement of cell-containing media within the hollow fibers.

The rotational and/or lateral movement of the rocking device can reduce the settling of cells within the device and reduce the likelihood of cells becoming trapped within a portion of the bioreactor 400. The rate of cells settling in the cell growth chamber (e.g., bioreactor 400) is proportional to the density difference between the cells and the suspension media according to Stoke's Law. In certain embodiments, a 180 degree rotation (fast) with a pause (having a total combined time of 30 seconds) repeated as described above keeps non-adherent red blood cells suspended. A minimum rotation of about 180 degrees is performed in some embodiments; however, one could use rotation of up to 360 degrees or greater in other embodiments. Different rocking components can be used separately, or can be combined in any combination. For example, a rocking component that rotates bioreactor 400 around central axis 410 can be combined with the rocking component that rotates bioreactor 400 around axis 412. Likewise, clockwise and counterclockwise rotation around different axes can be performed independently in any combination.

It is noted that the rocking devices, and their components, described above, may be implemented in embodiments using any appropriate structure. For example, in embodiments, one or more motors may be used as rocking devices, or components (e.g. 402 and 404) of rocking devices. In one embodiment, the rocking devices may be implemented using embodiments shown and described in U.S. Pat. No. 8,399,245 entitled ROTATION SYSTEM FOR CELL GROWTH CHAMBER OF A CELL EXPANSION SYSTEM AND METHOD OF USE THEREFOR, issued Mar. 19, 2013, which is hereby incorporated by reference in its entirety as if set forth herein in full.

Figure 2A:
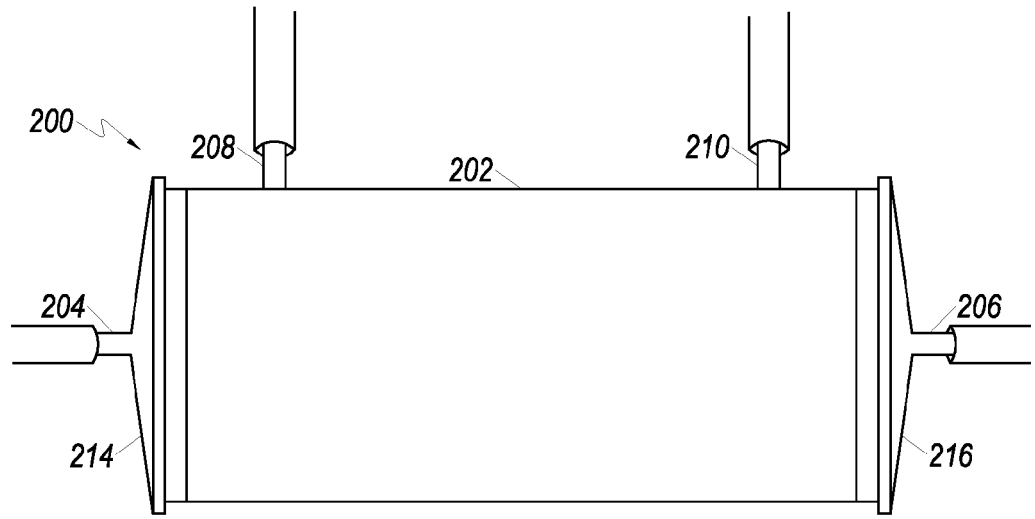
FIG. 2A depicts a side view of an embodiment of a hollow fiber cell growth chamber.
Figure 2B:
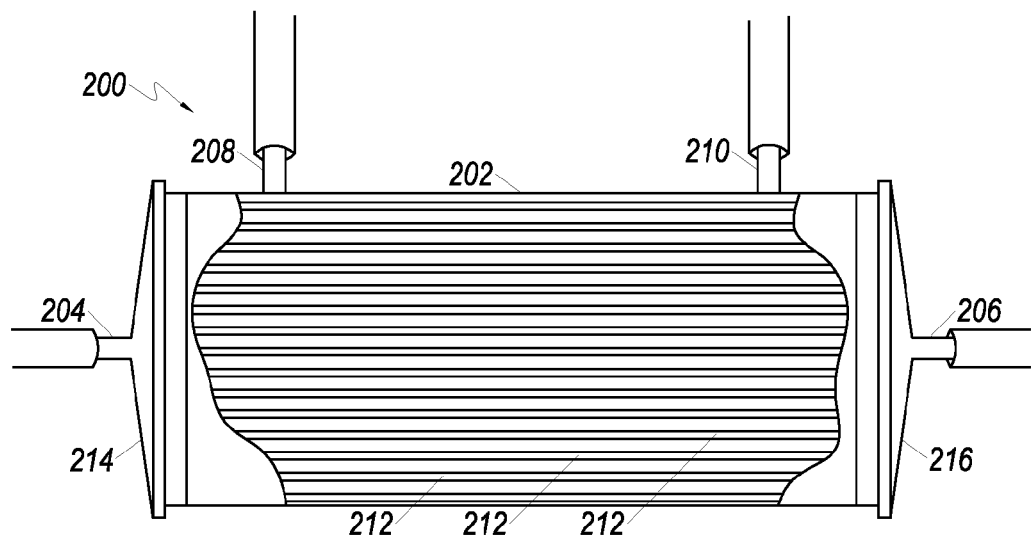
FIG. 2B depicts a cut-away side view of the embodiment of the hollow fiber cell growth chamber illustrated in FIG. 2A.

An embodiment of a cell growth chamber is depicted in FIGS. 2B and 2A, which depicts a cut-away and side view of a hollow fiber cell growth chamber 200, which may be referred to as a "bioreactor." Cell growth chamber 200 is bounded by cell growth chamber housing 202. Cell growth chamber housing 202 further includes four openings, or ports: inlet port 204, outlet port 206, inlet port 208, and outlet port 210.

Fluid in the first circulation path enters cell growth chamber 200 through inlet port 204, passes into and through the intracapillary side of a plurality of hollow fibers 212 (referred to in various embodiments as the intracapillary ("IC") side or "IC space" of a hollow fiber membrane), and out of cell growth chamber 200 through outlet port 206. The terms "hollow fiber," "hollow fiber capillary," and "capillary" are used interchangeably. A plurality of hollow fibers 212 are collectively referred to as a "membrane." Fluid in the second circulation path flows in the cell growth chamber through inlet port 208, comes in contact with the outside of the hollow fibers 212 (referred to as the "EC side" or "EC space" of the membrane), and exits cell growth chamber 200 via outlet port 210. Cells can be contained within the first circulation path or second circulation path, and can be on either the IC side or EC side of the membrane.

Although cell growth chamber housing 202 is depicted as cylindrical in shape, it can have any other shape known in the art. Cell growth chamber housing 202 can be made of any type of biocompatible polymeric material. Various other cell growth chamber housings may differ in shape and size.

Those of skill in the art will recognize that the term cell growth chamber does not imply that all cells being grown or expanded in a CES are grown in the cell growth chamber. In many embodiments, adherent cells can adhere to membranes disposed in the growth chamber, or may grow within the associated tubing. Non-adherent cells (also referred to as "suspension cells") can also be grown. Cells can be grown in other areas within the first or second fluid circulation path.

For example, the ends of hollow fibers 212 can be potted to the sides of the cell growth chamber 200 by a connective material (also referred to herein as "potting" or "potting material"). The potting can be any suitable material for binding the hollow fibers 212, provided that the flow of media and cells into the hollow fibers is not obstructed and that liquid flowing into the cell growth chamber 200 through the IC inlet port flows only into the hollow fibers 212. Exemplary potting materials include, but are not limited to, polyurethane or other suitable binding or adhesive components. In various embodiments, the hollow fibers 212 and potting may be cut through perpendicular to the central axis of the hollow fibers 212 at each end to permit fluid flow into and out of the IC side. End caps 214 and 216 are disposed at the end of the cell growth chamber.

Fluid entering cell growth chamber 200 via inlet port 208 is in contact with the outside of hollow fibers 212. This portion of the hollow fiber cell growth chamber is referred to as the "extracapillary (EC) space." Small molecules (e.g. water, oxygen, lactate, etc.) can diffuse through the hollow fibers 212 from the interior of the hollow fiber to the EC space, or from the EC space to the IC space. Large molecular weight molecules such as growth factors are typically too large to pass through the hollow fibers 212, and remain in the IC space of the hollow fibers. In embodiments in which cells are grown in the IC space, the EC space is used as a medium reservoir to supply nutrients to the cells and remove the byproducts of cellular metabolism. The media may be replaced as needed. Media may also be circulated through an oxygenator to exchange gasses as needed.

In various embodiments, cells can be loaded into the hollow fibers 212 by any of a variety of methods, including by syringe. The cells may also be introduced into the cell growth chamber 200 from a fluid container, such as a bag, which may be fluidly associated with the cell growth chamber.

Hollow fibers 212 are configured to allow cells to grow in the intracapillary space (i.e. inside the hollow fiber lumen) of the fibers. Hollow fibers 212 are large enough to allow cell adhesion in the lumen without substantially impeding the flow of media through the hollow fiber lumen. In various embodiments, the inner diameter of the hollow fiber can be greater than or equal to about 10000, about 9000, about 8000, about 7000, about 6000, about 5000, about 4000, about 3000, about 2000, about 1000, about 900, about 800, about 700, about 650, about 600, about 550, about 500, about 450, about 400, about 350, about 300, about 250, about 200, about 150, or even about 100 microns. Likewise, the outer diameter of the hollow fiber can be less than or equal to about 10000, about 9000, about 8000, about 7000, about 6000, about 5000, about 4000, about 3000, about 2000, about 1000, about 900, about 800, about 700, about 650, about 700, about 650, about 600, about 550, about 500, about 450, about 400, about 350, about 300, about 250, about 200, about 150, or even about 100 microns. The hollow fiber wall thickness should be sufficient to allow diffusion of small molecules, in some embodiments.

Any number of hollow fibers can be used in a cell growth chamber, provided the hollow fibers can be fluidly associated with the inlet and outlet ports of the cell growth chamber. In various embodiments, the cell growth chamber can include a number of hollow fibers greater than or equal to about 1000, about 2000, about 3000, about 4000, about 5000, about 6000, about 7000, about 8000, about 9000, about 10000, about 11000 or about 12000. In other embodiments, the cell growth chamber can include a number of hollow fibers less than or equal to about 12000, about 11000, about 10000, about 9000, about 8000, about 7000, about 6000, about 5000, about 4000, about 3000, or even about 2000. In other various embodiments, the length of the hollow fibers can be greater than or equal to about 100, about 200, about 300, about 400, about 500, about 600, about 700, about 800, or about 900 millimeters. In embodiments, the cell growth chamber contains about 9000 hollow fibers that have an average length of about 295 mm, an average inner diameter of 215 microns, and an average outer diameter of about 315 microns.

Hollow fibers can be constructed of any material capable of forming a size sufficient to form fibers capable of transporting liquid from the cell growth chamber inlet port to the cell growth chamber outlet port. In various embodiments, the hollow fibers can be constructed from plastic adherent materials capable of binding to certain types of cells, such as adherent stem cells (e.g. MSCs). In various other embodiments, hollow fibers can be treated with compounds such as fibronectin to form adherent surfaces.

In certain embodiments, the hollow fibers may be made of a semi-permeable, biocompatible polymeric material. One such polymeric material which can be used is a blend of polyamide, polyarylethersulfone and polyvinylpyrrolidone (referred to herein as "PA/PAES/PVP"). The semi-permeable membrane allows transfer of nutrients, waste and dissolved gases through the membrane between the EC space and IC space. In various embodiments, the molecular transfer characteristics of the hollow fiber membranes are chosen to minimize loss of expensive reagents necessary for cell growth such as growth factors, cytokines etc. from the hollow fiber, while allowing metabolic waste products to diffuse through the membrane into the hollow fiber lumen side to be removed.

In certain variations, one outer layer of each PA/PAES/PVP hollow fiber may be characterized by a homogenous and open pore structure with a defined surface roughness. The openings of the pores may be in the size range of about 0.5 to about 3 microns, and the number of pores on the outer surface of the fibers may be in the range of about 10,000 to about 150,000 pores per $mm^2$. This outer layer has a thickness of about 1 to about 10 microns. The next layer in each hollow fiber may be a second layer having the form of a sponge structure and, in embodiments have a thickness of about 1 to about 15 microns. This second layer may serve as a support for the outer layer. A third layer next to the second layer may have the form of finger-like structures. This third layer provides mechanical stability and a high void volume which gives the membrane a low resistance to transporting molecules through the membrane. During use, the finger-like voids are filled with fluid and the fluid gives a lower resistance for diffusion and convection than a matrix with a sponge-filled structure having a lower void volume. This third layer may have a thickness of about 20 to about 60 microns.

In further embodiments, the hollow fiber membrane can include between about 65 to about 95% by weight of at least one hydrophobic polymer and between about 5 to about 35% by weight of at least one hydrophilic polymer. The hydrophobic polymer may be chosen from the group consisting of polyamide (PA), polyaramide (PAA), polyarylethersulphone (PAES), polyethersulphone (PES), polysulphone (PSU), polyarylsulphone (PASU), polycarbonate (PC), polyether, polyurethane (PUR), polyetherimide and copolymer mixtures of any of the above polymers, such as polyethersulphone or a mix of polyarylethersulphone and polyamide. In additional embodiments, the hydrophilic polymer may be chosen from the group consisting of polyvinylpyrrolidone (PVP), polyethylene glycol (PEG), polyglycolmonoester, water soluble cellulosic derivates, polysorbate and polyethylene-polypropylene oxide copolymers.

Depending upon the type of cells to be expanded in the cell growth chamber, the polymeric fibers may be treated with a substance, such as fibronectin, to enhance cell growth and/or adherence of the cells to the membrane.

Figure 3:
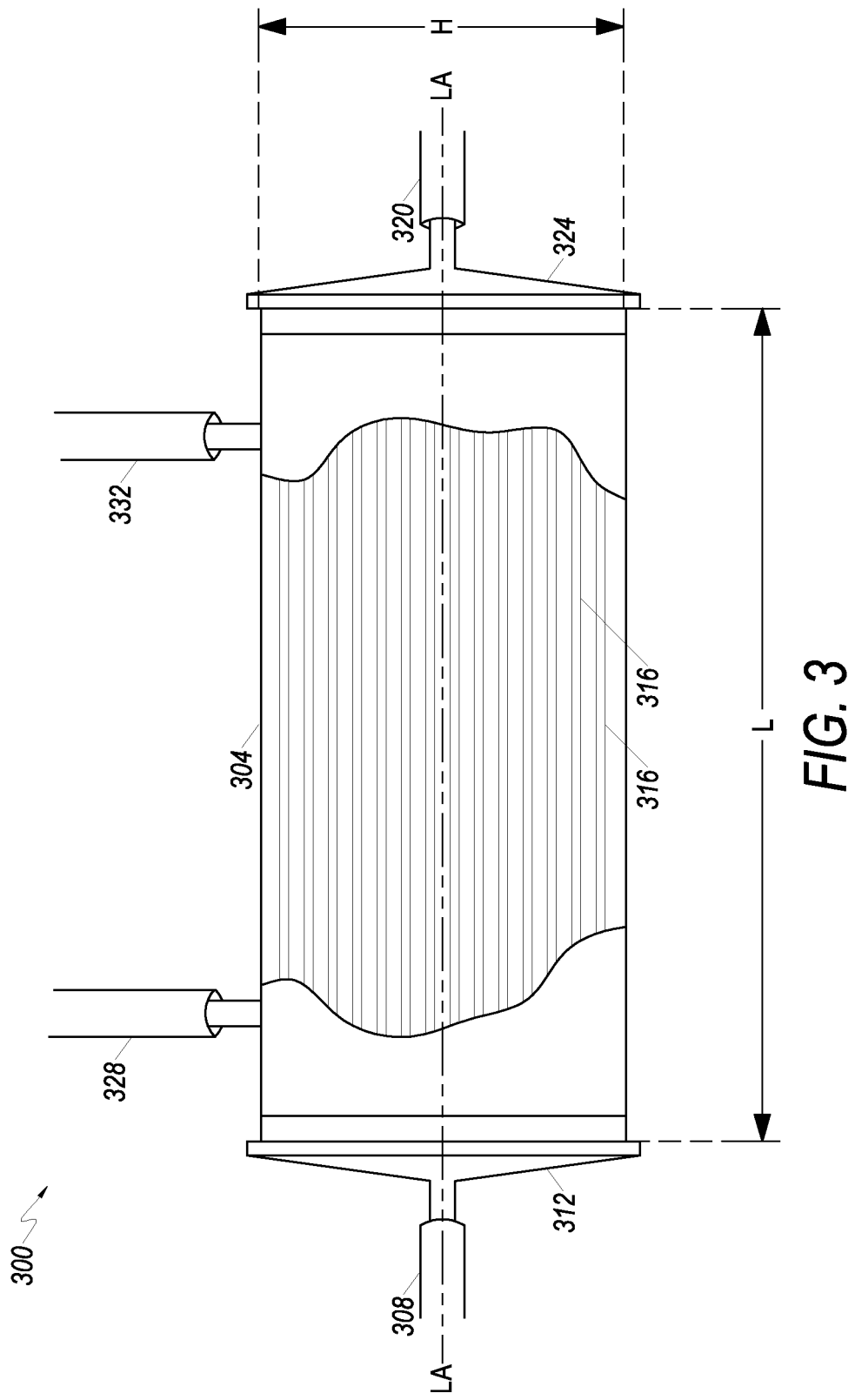
FIG. 3 depicts a cut-away side view of another embodiment of a bioreactor showing circulation paths through the bioreactor.

With reference now to FIG. 3, an example of another cell growth chamber, bioreactor 300, is shown in a cut-away side view. Bioreactor 300 has a longitudinal axis LA-LA and includes bioreactor housing 304. In at least one embodiment, bioreactor housing 304 includes four openings or ports: IC inlet port 308, IC outlet port 320, EC inlet port 328, and EC outlet port 332.

Fluid in a first circulation path enters bioreactor 300 through IC inlet port 308 at a first longitudinal end 312 of the bioreactor 300, passes into and through the intracapillary side (referred to in various embodiments as the intracapillary ("IC") side or "IC space" of a hollow fiber membrane) of a plurality of hollow fibers 316, and out of bioreactor 300 through IC outlet port 320 located at a second longitudinal end 324 of the bioreactor 300. Fluid in a second circulation path flows in the bioreactor 300 through EC inlet port 328, comes in contact with the extracapillary side or outside (referred to as the "EC side" or "EC space" of the membrane) of the hollow fibers 316, and exits bioreactor 300 via EC outlet port 332. Fluid entering bioreactor via an EC inlet port 328 is in contact with the outside of the hollow fibers. Small molecules (e.g. water, oxygen, lactate, etc.) can diffuse through the hollow fibers from the interior of the hollow fiber to the EC space, or from the EC space to the IC space. Large molecular weight molecules such as growth factors are typically too large to pass through the hollow fibers, and remain in the IC space of the hollow fibers. The media may be replaced as needed. Media may also be circulated through an oxygenator to exchange gasses as needed. Cells can be contained within the first circulation path and/or second circulation path, and can be on either the IC side and/or EC side of the membrane. By way of example and not limitation, in one embodiment, the bioreactor 300 may include about 11520 fibers that have about $215 \times 10^{-6}$ m inner diameters (ID).

Although bioreactor housing 304 is depicted as cylindrical in shape, it could have a variety of shapes, such as a rectangular cube. Bioreactor housing 304 can be made of any type of biocompatible polymeric material, including a substantially transparent material that permits an observer to see one or more of the plurality of hollow fibers 316, as well as fluid residing within the bioreactor housing 304. Various other bioreactor housings may differ in shape and size.

Figure 4:
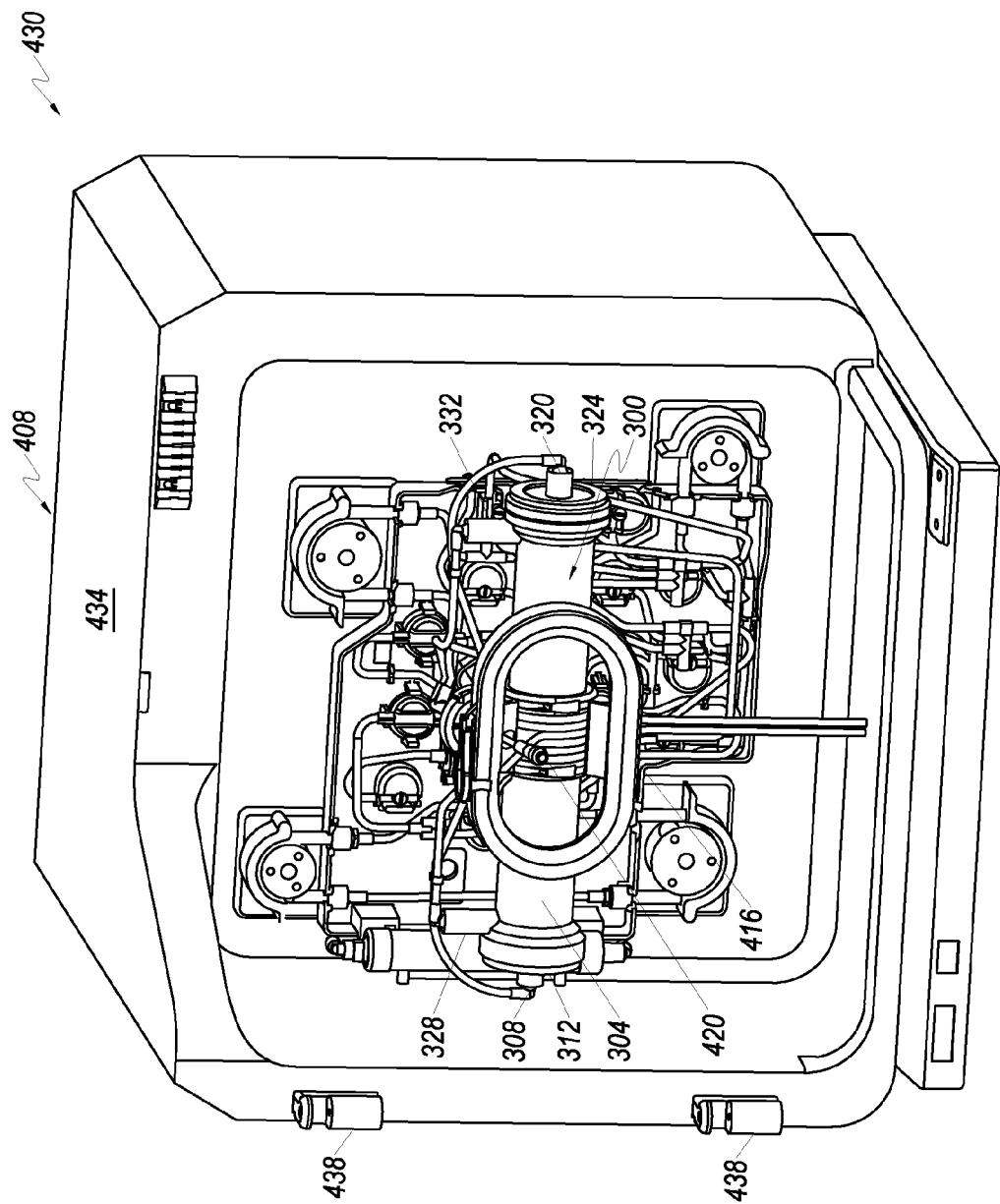
FIG. 4 illustrates a perspective view of a portion of a CES, including a detachably attached bioreactor, according to an embodiment.

Referring now to FIG. 4, a portion of a CES 430 is shown in perspective view, and includes a back portion 434 of body 408 of the CES 430. For clarity, the front portion the body 408 is not shown; however, the front portion is attached to the back portion 434, such as by hinges 438, thereby allowing the front portion to comprise a door or hatch that can be opened to access the bioreactor 300 of the CES 430. Attached to the bioreactor 300 may be a spool 416 for tubing and a sampling port 420. The environment in the vicinity of the bioreactor 300 is temperature controlled to provide appropriate conditions for cell growth.

Figure 5:
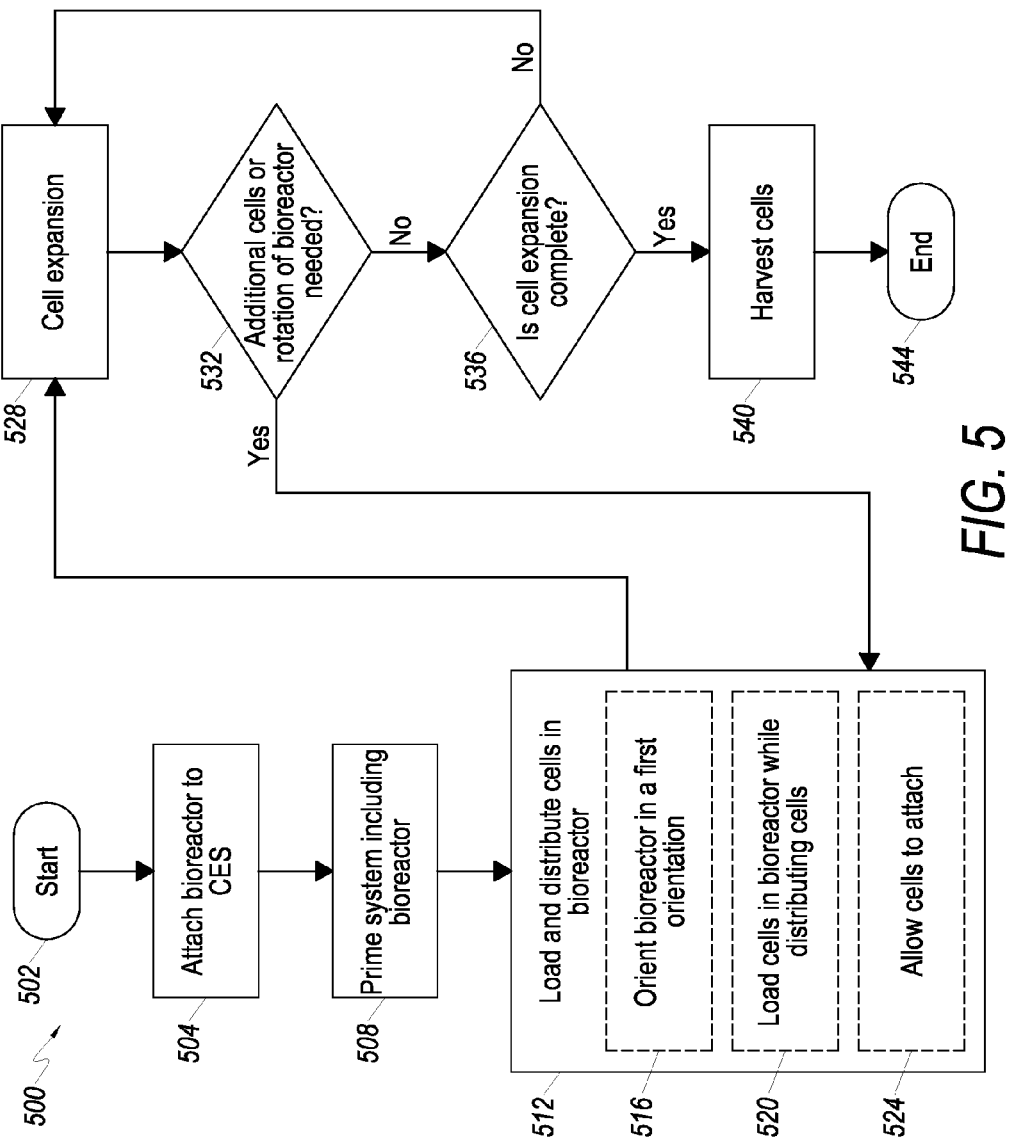
FIG. 5 illustrates a flow chart of a method for expanding cells in a CES according to an embodiment.

Referring now to FIG. 5, a flow chart 500 is shown that depicts one embodiment of a cell expansion process associated with using a CES, including the steps associated with loading and distributing cells in a bioreactor (e.g., bioreactor 300), as further described herein. Although features of a CES (e.g., CES 430) are described as performing some of the steps of flow chart 500, the present invention is not limited thereto. Indeed, other CES's with different features, not described herein or described above (e.g., CES's 10, 800, or 900), may be utilized in some embodiments. Accordingly, reference to features of CES 430 such as bioreactor 300 are provided for illustrative purposes only, and the flow chart 500 is not limited to use with any specific CES.

Flow chart 500 starts at 502 and passes to 504 where a bioreactor 300 and any associated tubing and related structures are connected to the body 408 to provide an operable CES 430. Once connected to the body 408, the bioreactor 300 and its associated tubing and related structures are primed at 508 using an appropriate priming fluid, such as saline. At 512, cells are loaded and distributed in the bioreactor 300.

The loading and distributing of cells in embodiments involves a number of substeps, for example, in some embodiments step 512 additionally includes optional steps of orienting the bioreactor 300 in a first orientation at optional substep 516, and then loading and distributing the cells in the bioreactor 300 at optional substep 520. At optional substep 524, cells may be allowed to attach to the bioreactor.

Following loading and distributing cells in the bioreactor 300, the cells undergo expansion at 528. That is, the cells within the bioreactor 300 are allowed to expand, i.e., grow and/or multiply. At 532, an assessment is made as to whether additional cells need to be added to the bioreactor 300 and/or whether the bioreactor 300 needs to be rotated to distribute cells within the bioreactor 300. If additional cells need to be loaded into the bioreactor 300 and/or if cells need to be distributed in the bioreactor 300, then the flow chart 500 returns to step 512. If cells do not need to be added and/or the bioreactor 300 does not need to be rotated, then at 536 an assessment is made as to whether the cell expansion process 528 is complete. As used herein, the cell expansion process is determined to be complete if a sufficient number of cells and/or change in cell characteristics have been achieved. If the cell expansion process 528 is complete, the cells are harvested at 540. If cell expansion process 528 is not complete, then the cell expansion process at 528 is allowed to continue. Flow chart 500 ends at 544.

Figure 6:
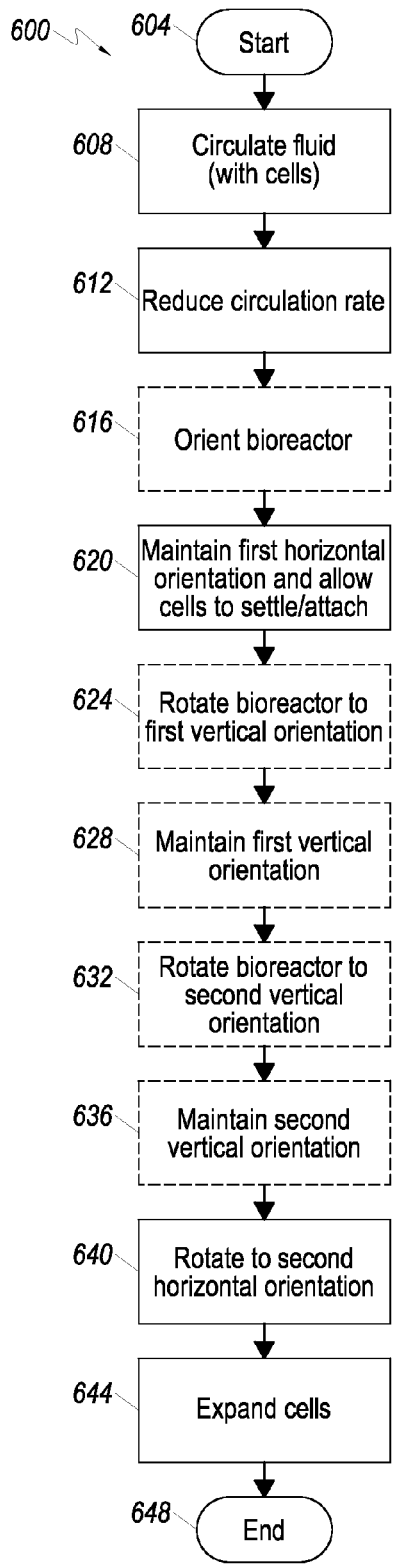
FIG. 6 illustrates a flow chart of a process for loading, distributing, attaching, and expanding cells that includes steps that may be used in the method of the flow chart illustrated in FIG. 5 in some embodiments.
Figure 7:
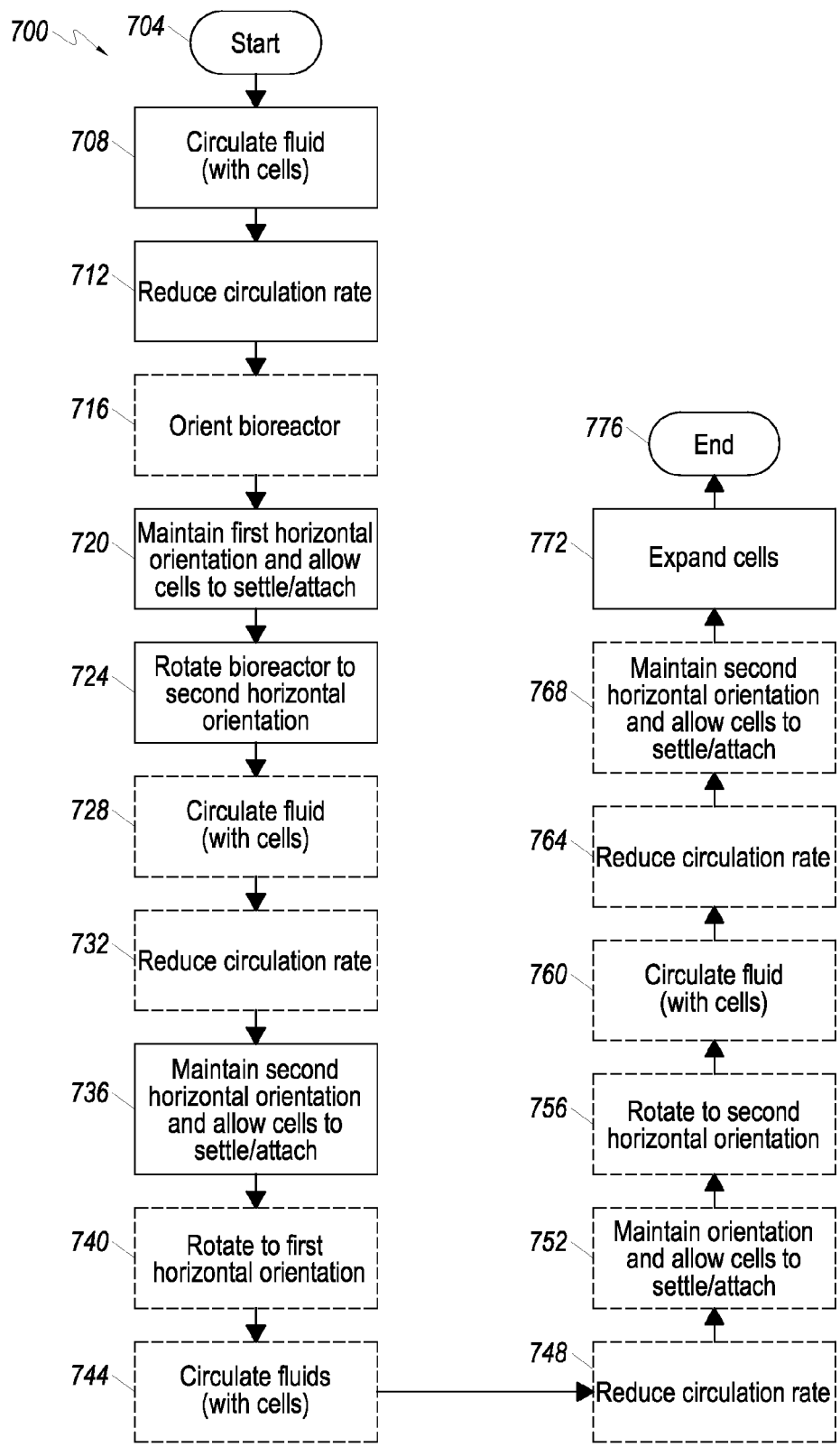
FIG. 7 is a flow chart of a process for loading, distributing, attaching, and expanding cells that includes steps that may be used in the method of the flow chart illustrated in FIG. 5 in some embodiments.

Additional detail is now provided regarding processes that may be used to load, distribute and expand cells in a bioreactor and CES's, e.g., steps 512 and 528 (FIG. 5), in some embodiments. FIGS. 6 and 7 illustrate flow charts of some processes that may be used to load, distribute, attach and expand cells. These processes may be performed as part of a process of flow chart 500, e.g., sub-steps of steps described above, e.g., steps 512 and 528. In other embodiments, the processes described by flow chart 600 and 700 may be performed without regard to the steps described in flow chart 500. Additionally, the steps in flow charts 600 and 700 may be described below as being performed by, or with respect to, a CES or portions thereof (e.g., CES's 10, 800, 900), including components (e.g., motors used as rocking components 402 and 404), a bioreactor (e.g., bioreactors 24, 300, 400, 801, or 908); or portions of a bioreactor. This description is not intended to limit flow charts 600 and 700, which in embodiments may have their steps performed by, or with respect to, other systems, devices, components, or features.

Flow chart 600 starts at 604, and passes to step 608 where fluid that includes cells may be circulated through a bioreactor such as bioreactor 300 (see FIGS. 3 and 8-12). In embodiments, step 608 may involve activating one or more pumps to circulate fluid through the bioreactor 300. For example, an IC circulation pump (e.g., 812 or 911) may be activated to circulate fluid through the IC side of bioreactor 300 at a first circulation flow rate. In at least one embodiment, fluid carrying the cells may pass through hollow fibers of the bioreactor 300 from the IC side to the EC side. In other embodiments, cells may be loaded into the EC side of the bioreactor 300 and have the fluid carrying the cells pass from the EC side to the IC side. In these embodiments, an EC circulation pump (e.g., 828 or 974) may be activated to circulate fluid through the EC side of bioreactor 300 at a first circulation flow rate.

Step 608 may in some embodiments involve also rotating the bioreactor 300 in a particular sequence to facilitate distribution of the cells through the bioreactor 300 and circulation paths of the CES to which the bioreactor 300 may be fluidly associated. Examples of embodiments for rotating bioreactor 300 in a particular sequence to facilitate distribution of the cells during circulation or loading is described in U.S. patent application Ser. No. 12/968,483, filed on Dec. 15, 2010, entitled "METHOD OF LOADING AND DISTRIBUTING CELLS IN A BIOREACTOR OF A CELL EXPANSION SYSTEM," which is hereby incorporated by reference in its entirety as if set forth herein in full. In other embodiments, the circulating step 608 may involve rotating the bioreactor 300 for some periods of time, but maintaining the bioreactor 300 stationary for other periods of time.

After step 608, the fluid circulation rate is reduced at step 612. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers 316 of bioreactor 300. In embodiments, step 612 may involve stopping or turning off one or more pumps used in step 608 to circulate the fluid.

Flow passes from step 612 to optional step 616, which may be performed to orient a bioreactor, e.g. bioreactor 300 to an initial orientation. In embodiments, a bioreactor may already be oriented in an initial orientation, which would make step 616 unnecessary. When performed, step 616 may be performed by one or more motors in embodiments.

Figure 8:
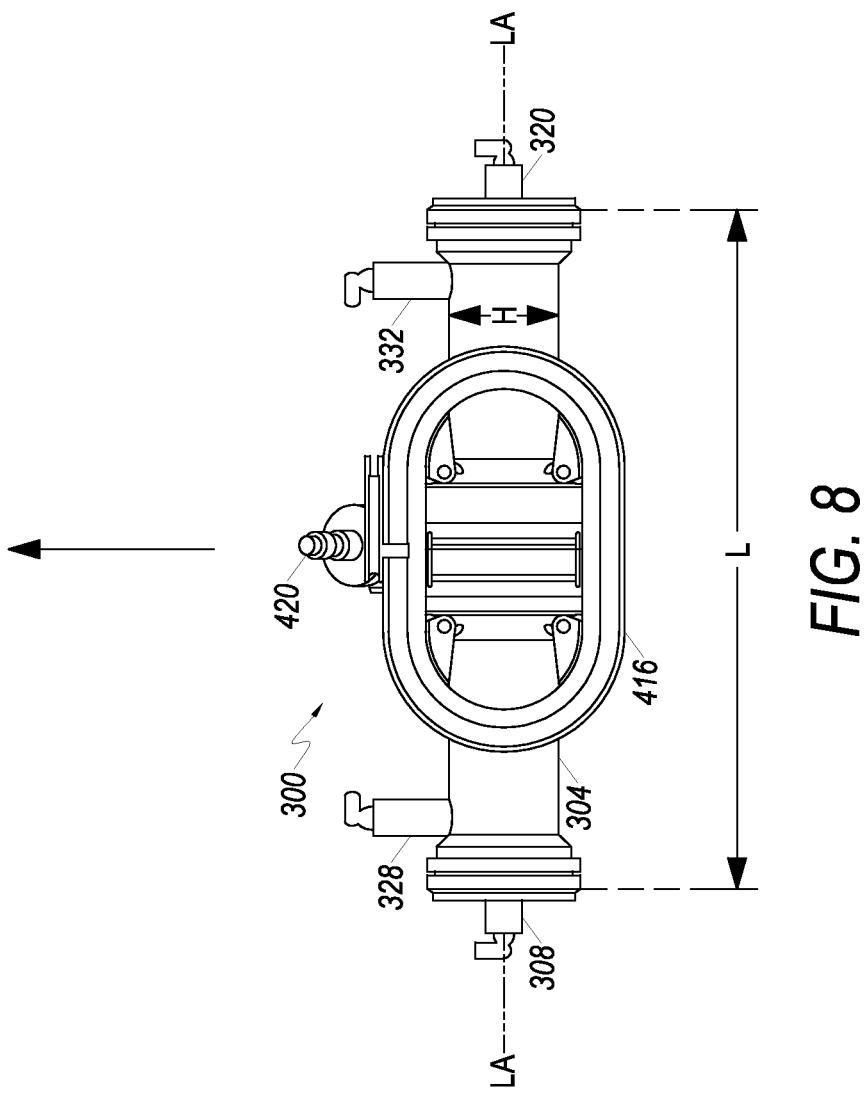
FIG. 8 illustrates a front elevation view of an embodiment of a bioreactor in a first orientation.

Referring now to FIGS. 8-12, a bioreactor 300 is shown in FIG. 8 positioned in an initial orientation. As part of optional step 616, bioreactor 300 may be oriented with its longitudinal axis LA-LA in a starting orientation, such as, for example, a first horizontal orientation as shown in FIG. 8.

Flow passes from 616, to step 620 where the bioreactor is maintained at a first orientation to allow cells to settle and in some embodiments attach to a first portion of bioreactor 300. Step 620 is performed for a first predetermined period of time.

Figure 13A:
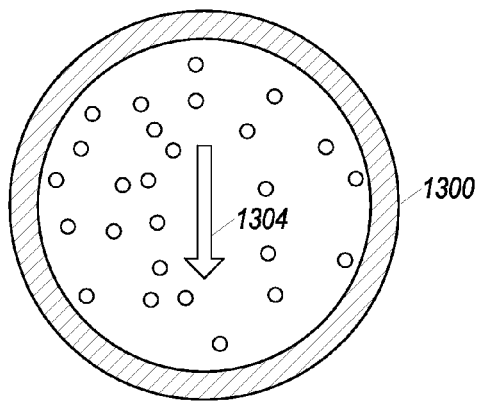
FIGS. 13A-13C illustrate a cross section (perpendicular to a central axis) of a hollow fiber that may be part of a bioreactor as it progresses through steps of a process for distributing, attaching, and expanding cells in the bioreactor according to an embodiment.
Figure 13B:
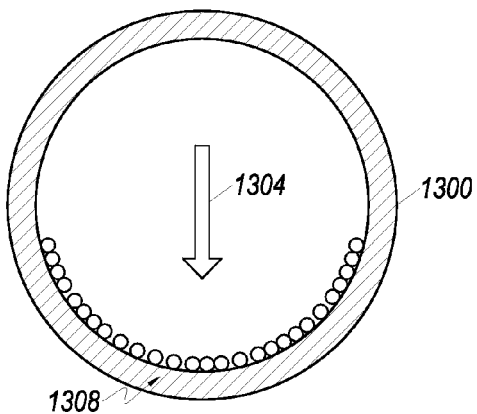
Figure 13C:
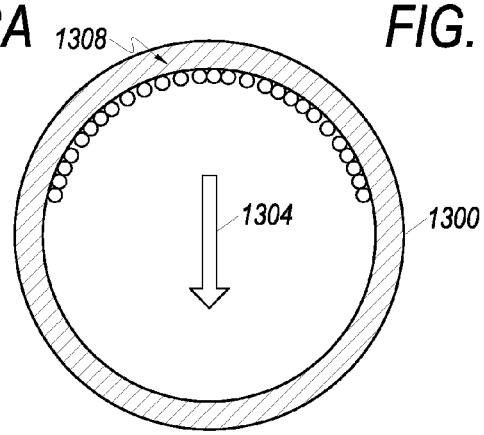

Referring now to FIGS. 13A-13C, these figures illustrate a cross-section of a hollow fiber 1300 (taken perpendicular to a central axis of the hollow fiber 1300 and a central axis of bioreactor 300) that may be one of the hollow fibers 316 of bioreactor 300. These figures illustrate the possible locations of cells within the hollow fibers 316 during some step of flow chart 600. As illustrated in FIG. 13A, before the circulation rate is reduced at step 612, cells within individual hollow fiber 1300 may be distributed, in embodiments evenly, throughout the volume of hollow fiber 1300. When the circulation rate is reduced, the cells may begin to be influenced by gravity 1304 and begin to settle.

In embodiments, with the bioreactor 300 in the first horizontal orientation (FIG. 8), the cells within bioreactor 300 are allowed to settle onto a first portion of the bioreactor. As illustrated in FIG. 13B, the first portion of bioreactor 300 may include at least a portion 1308 of hollow fiber 1300. In embodiments, the cells will be allowed to settle for a first predetermined period of time (step 620 in flow chart 600) that may be selected to not only allow the cells to settle, but also to attach to portion 1308 of the hollow fiber 1300.

In some embodiments, the first predetermined period of time may be long enough in duration merely to allow the cells to settle and attach to portion 1308. In these embodiments, the cells may only need to travel the distance of the inner diameter of hollow fiber 1308. For example, in embodiments where the hollow fiber has an inner diameter of between about 150 microns and about 300 microns, the first predetermined period of time may be less than about 20 minutes, less than about 15 minutes, or even less than about 10 minutes. In other embodiments, the first predetermined period of time may be greater than about 1 minute, greater than about 2 minutes, greater than about 3 minutes, or even greater than about 4 minutes. In one embodiment, the first period of time may be between about 3 minutes and about 8 minutes, such as about 5 minutes.

In other embodiments, the first predetermined period of time may be long enough in duration to not only allow cells to settle and attach to a hollow fiber, it may be long enough in duration to allow attached cells to grow. In these embodiments, the cells may grow laterally since either lateral direction may provide the least resistance. In other words, because the cells on portion 1308 would be growing against the force of gravity 1304 if they grew upward on the fiber wall, it is believe that in embodiments, they may grow laterally, at least initially. In these embodiments, when the cells are allowed to grow after attachment, the first predetermined period of time may be greater than about 5 hours, greater than about 10 hours, greater than about 15 hours, greater than about 20 hours, or even greater than about 24 hours. In other embodiments, the first predetermined period of time may be less than about 60 hours, less than about 55 hours, less than about 50 hours, or even less than about 45 hours. In one embodiment, the predetermined period of time may be between about 10 hours and about 48 hours.

Figure 9:
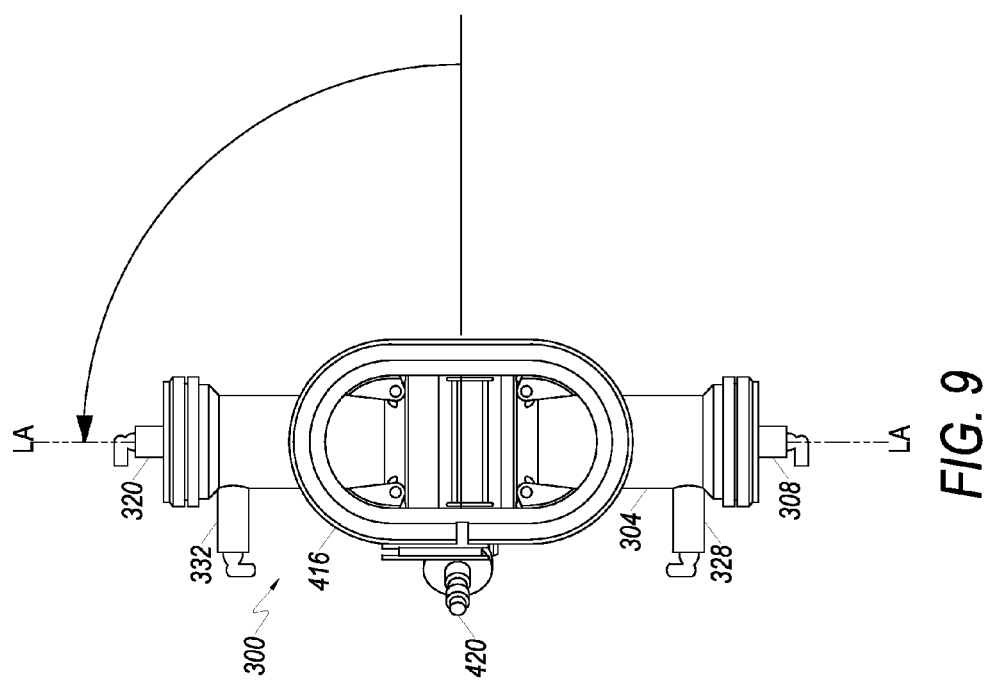
FIG. 9 illustrates a front elevation view of the bioreactor of FIG. 8, wherein the bioreactor is shown rotated about 90 degrees from the view of FIG. 8.
Figure 10:
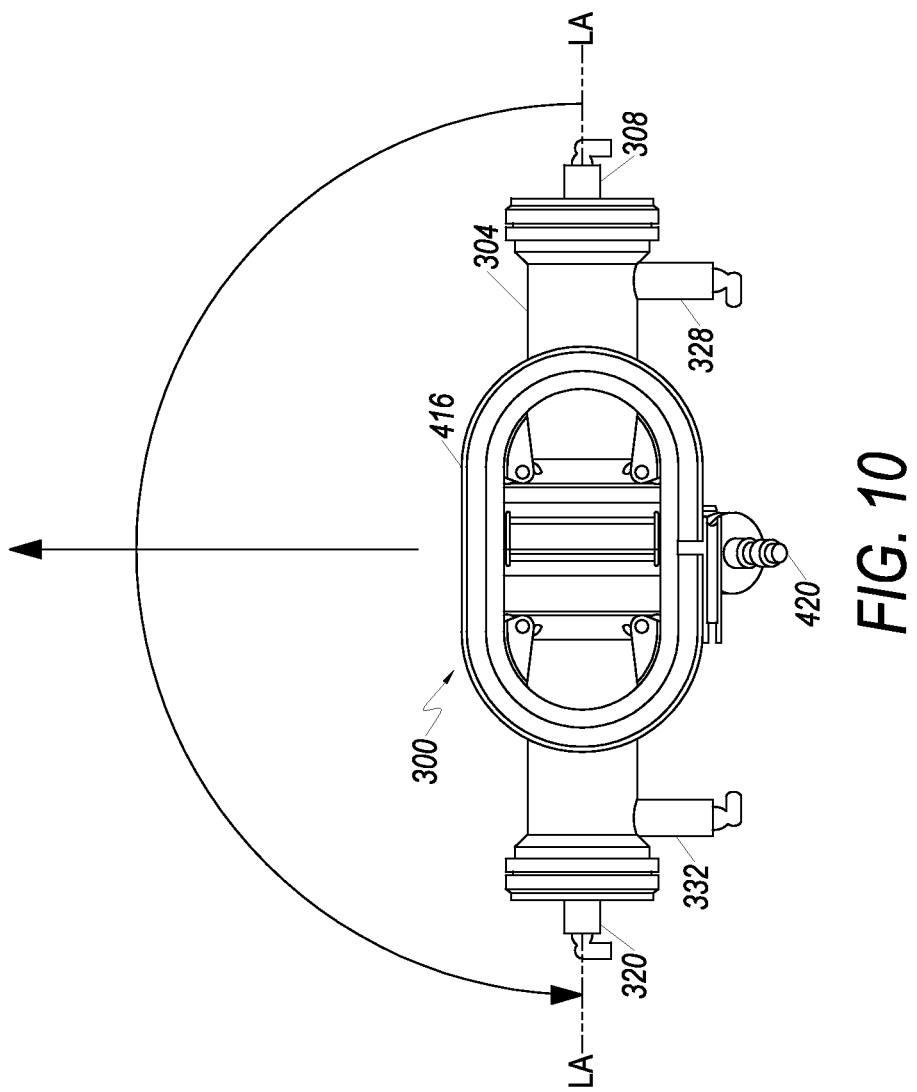
FIG. 10 is a front elevation view of the bioreactor of FIG. 8, wherein the bioreactor is shown rotated about 180 degrees from the view of FIG. 8

Referring back to FIG. 6, in some embodiments, after step 620, flow passes to step 640, where the bioreactor 300 is rotated to a second horizontal orientation that is about 180 degrees from the first horizontal orientation. As shown in FIGS. 8-10, the bioreactor may be rotated by first being rotated from its first horizontal orientation (FIG. 8) to a first vertical orientation, which is about 90 degrees from the first horizontal orientation, e.g. axis LA LA in a vertical orientation (FIG. 9). Bioreactor 300 may then be rotated another 90 degrees (FIG. 10) to complete the rotation to the second horizontal orientation.

In embodiments, after rotation to the second horizontal orientation, flow 600 may pass to step 644, where the cell expansion is then performed with the bioreactor 300 in the second horizontal orientation. FIG. 13C illustrates that in the second horizontal orientation, the cells attached to hollow fiber 1300 are now positioned on a top inside portion of the hollow fiber 1300. Step 644 may involve a number of substeps, such as circulating fluid into the bioreactor to feed and provide nutrients to the cells attached in the bioreactor. As can be appreciated, step 644 may also involve providing oxygen to the cells so that they may multiply. Several other parameters in the bioreactor may be controlled in order to optimize the expansion, i.e. growth of the cells. In some embodiments, step 644 may include circulating fluid to feed the cells for about 24 hours, about 36 hours, about 48 hours, about 60 hours, or even about 72 hours. In some embodiments, the feeding of the cells as part of step 644 may be performed for less than about 120 hours, less than about 108 hours, less than about 96 hours, less than about 84 hours, or even less than about 72 hours. Flow 600 may then end at 648.

Without being bound by theory, it is believed that in embodiments, the cell expansion is improved if the cells are grown as illustrated in FIG. 13C under the influence of gravity. The cells may in embodiments grow downward in the hollow fiber 1300, toward portions of the hollow fiber that do not have cells. It is believed that the cells may grow toward portions of the fiber that provide the least resistance, such as portions below the top portion 1308, see FIG. 13C. In embodiments, growing under the influence of gravity improves cell yield and reduces cell doubling time, as compared to conventional processes.

In other embodiments, flow 600 may include additional steps. For example, in some embodiments, after step 620, flow 600 may pass to step 624 where bioreactor 628 may be rotated to a vertical orientation. For example, bioreactor 300 may be rotated to a first vertical orientation as shown in FIG. 9. After step 624, flow may pass to step 628, where the bioreactor may be maintained in the first vertical orientation for a second predetermined period of time.

Figure 13D:
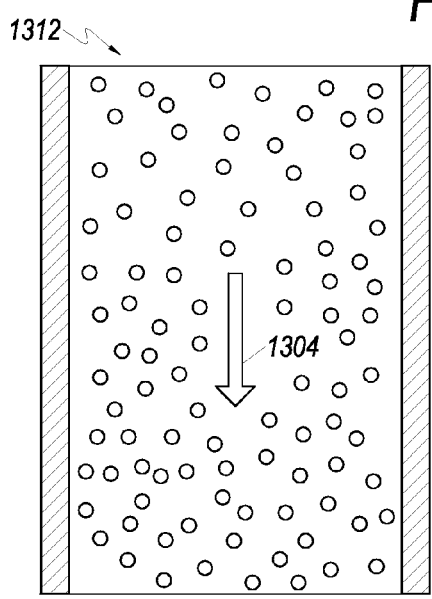
FIGS. 13D and 13E illustrate a cross section (parallel to a central axis) of a hollow fiber that may be part of a bioreactor as it progresses through steps of a process for expanding cells in the bioreactor according to an embodiment.
Figure 13E:
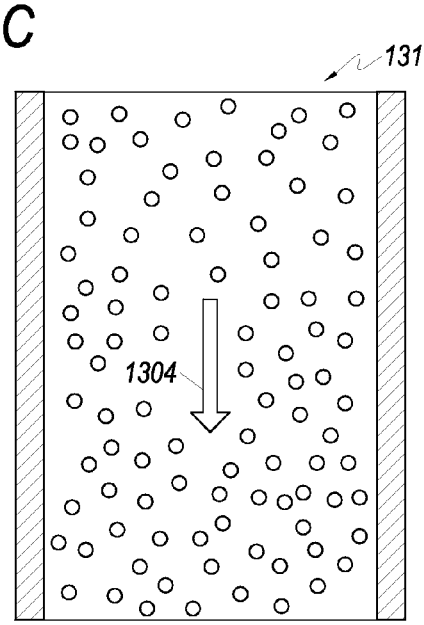

Referring now to FIGS. 13D and 13E, these figures illustrate a cross-section of a hollow fiber 1300 (taken parallel to a central axis of the hollow fiber 1300 and a central axis of bioreactor 300) that may be one of the hollow fibers 316 of bioreactor 300. FIGS. 13D and 13E illustrate hollow fiber 1300 after step 620, where cells have settled and attached to a portion of the fiber 1300. As shown in FIG. 13D, when bioreactor 300 is rotated to the first vertical orientation, a first end 1312 of hollow fiber 1300 is positioned above a second end 1316.

As noted above, without being bound by theory, it is believed that the cells that are attached to fiber 1300 will be influenced by gravity 1304 and begin to grow, i.e., expand, longitudinally toward end 1316. Therefore, in embodiments, step 628 (maintain first vertical orientation) is performed for a second predetermined period of time that may be long enough in duration to allow the cells to grow longitudinally. The second predetermined period of time may be in some embodiments, greater than about 5 hours, greater than about 10 hours, greater than about 15 hours, greater than about 20 hours, or even greater than about 24 hours. In other embodiments, the second predetermined period of time may be less than about 60 hours, less than about 55 hours, less than about 50 hours, or even less than about 45 hours. In one embodiment, the predetermined period of time may be between about 10 hours and about 48 hours.

Figure 12:
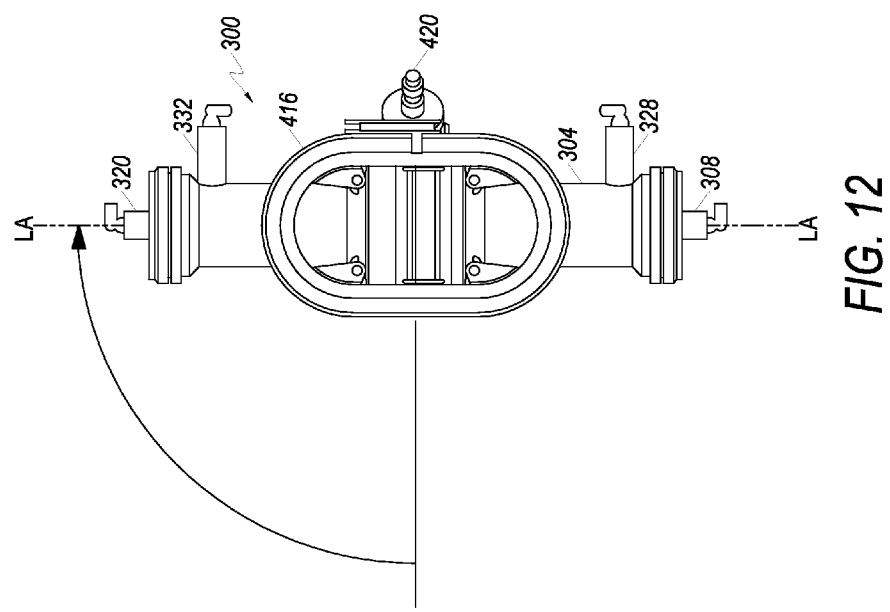
FIG. 12 illustrates a front elevation view of the bioreactor of FIG. 8, wherein the bioreactor is shown rotated about 90 degrees from the view of FIG. 8 and about 180 degrees from the view of FIG. 9.

After step 628, flow may pass to step 632, where the bioreactor may be rotated to a second vertical orientation. One example of bioreactor 300 in a second vertical orientation is shown in FIG. 12. After step 624, flow may pass to step 636, where the bioreactor may be maintained in the second vertical orientation for a third predetermined period of time.

Referring to FIG. 13E, this figure illustrates hollow fiber 1300 after step 632, where cells have settled and attached to a portion of the fiber 1300 and the bioreactor 300 has been rotated from a first vertical orientation to a second vertical orientation and is being maintained in the second vertical orientation. As shown in FIG. 13E, when bioreactor 300 is rotated to the second vertical orientation, the first end 1312 of hollow fiber 1300 is positioned below the second end 1316.

Similar to step 628 (maintain first vertical orientation), step 636 (maintain second vertical orientation) is performed because it is believed that in embodiments, the cells that are attached to fiber 1300 will be influenced by gravity 1304 and begin to grow, i.e., expand, longitudinally toward end 1312. Step 636 may be performed in embodiments for a third predetermined of period of time that may be long enough in duration to allow the cells to grow longitudinally toward end 1312 as shown in FIG. 13E. The third predetermined period of time may be in some embodiments, greater than about 5 hours, greater than about 10 hours, greater than about 15 hours, greater than about 20 hours, or even greater than about 24 hours. In other embodiments, the second predetermined period of time may be less than about 60 hours, less than about 55 hours, less than about 50 hours, or even less than about 45 hours. In one embodiment, the predetermined period of time may be between about 10 hours and about 48 hours.

Figure 11:
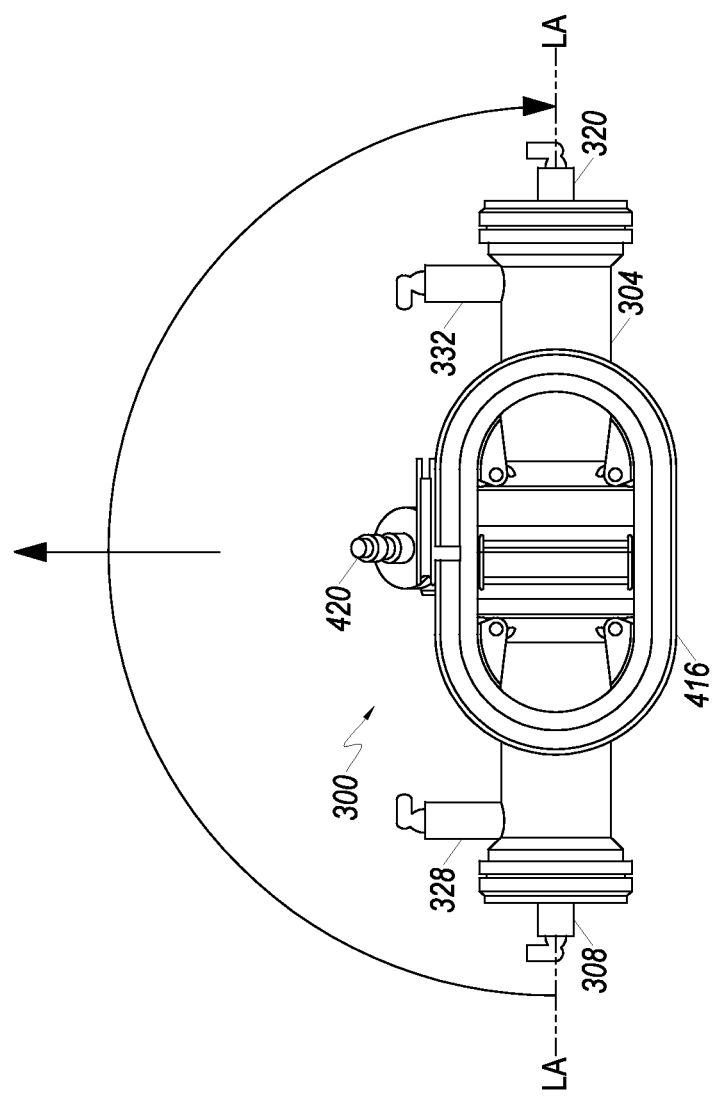
FIG. 11 is a front elevation view of the bioreactor of FIG. 8, wherein the bioreactor is shown rotated back to the original orientation shown in FIG. 8.

Referring back to flow chart 600, after step 636, flow may pass to step 640 where as described above, the bioreactor may be rotated to a second horizontal position as shown in FIG. 11. As described above, from step 640, flow 600 passes to 644 where the cells are expanded, i.e. multiplied. Flow then ends at 648.

Turning now to FIG. 7, flow 700 begins at 704 and passes to step 708 where fluid that includes cells may be circulated through a bioreactor such as bioreactor 300 (see FIGS. 3 and 8-12). In embodiments, step 708 may involve activating one or more pumps to circulate fluid through the bioreactor 300. For example, an IC circulation pump (e.g., 812 or 911) may be activated to circulate fluid through the IC side of bioreactor 300 at a first circulation flow rate. In at least one embodiment, fluid carrying the cells may pass through hollow fibers of the bioreactor 300 from the IC side to the EC side. In other embodiments, cells may be loaded into the EC side of the bioreactor 300 and have the fluid carrying the cells pass from the EC side to the IC side. In these embodiments, an EC circulation pump (e.g., 828 or 974) may be activated to circulate fluid through the EC side of bioreactor 300 at a first circulation flow rate.

In embodiments, the first circulation flow rate may be a relatively high flow rate. In embodiments, the first circulation flow rate may be less than about 500 ml/min, less than about 400 ml/min, or even less than about 300 ml/min. In other embodiments, the first circulation rate may be greater than about 50 ml/min, greater than about 100 ml/min, or even greater than about 150 ml/min. In one embodiment, the first circulation flow rate is between about 100 ml/min and about 300 ml/min, such as about 200 ml/min.

Step 708 may in some embodiments involve also rotating the bioreactor 300 in a particular sequence to facilitate distribution of the cells through the bioreactor 300 and circulation paths of the CES to which the bioreactor 300 may be fluidly associated. In other embodiments, the circulating step 708 may involve rotating the bioreactor 300 for some periods of time, but maintaining the bioreactor 300 stationary for other periods of time.

After step 708, the fluid circulation rate is reduced at step 712. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers 316 of bioreactor 300. In embodiments, step 712 may involve stopping or turning off one or more pumps used in step 708 to circulate the fluid.

Flow passes from step 712 to optional step 716, which may be performed to orient a bioreactor, e.g. bioreactor 300 to an initial orientation. In embodiments, a bioreactor may already be oriented in an initial orientation, which would make step 716 unnecessary. When performed, step 716 may in some embodiments be performed by one or more motors.

Referring now to FIGS. 8-12, a bioreactor 300 is shown in FIG. 8 positioned in an initial orientation. As part of optional step 716, bioreactor 300 may be oriented with its longitudinal axis LA-LA in a starting orientation, such as, for example, a first horizontal orientation as shown in FIG. 8.

Flow passes from 716, to step 720 where the bioreactor is maintained at a first orientation to allow cells to settle and in some embodiments attach to a first portion of bioreactor 300. Step 820 is performed for a first predetermined period of time.

Figure 14A:
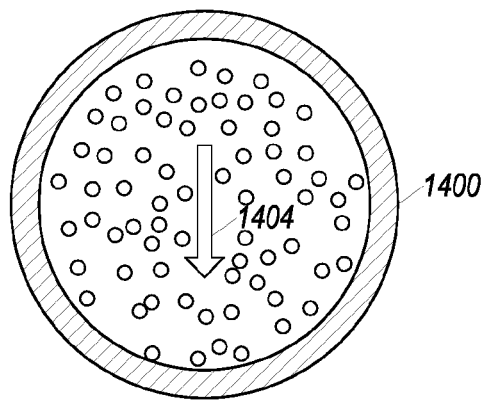
FIGS. 14A-14D illustrate a cross section (perpendicular to a central axis) of a hollow fiber that may be part of a bioreactor as it progresses through steps of a process for distributing, attaching, and expanding cells in the bioreactor according to another embodiment.
Figure 14B:
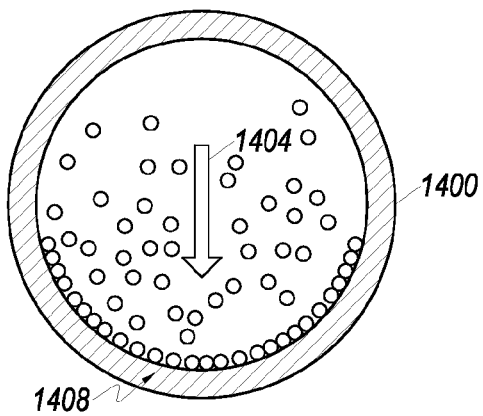
Figure 14C:
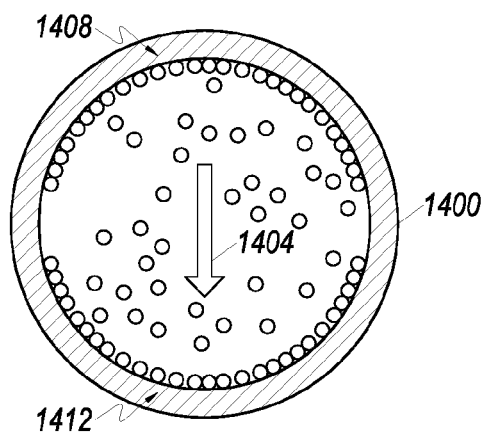
Figure 14D:
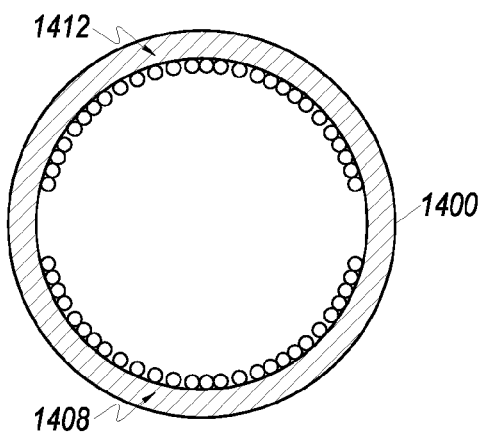
Figure 15A:
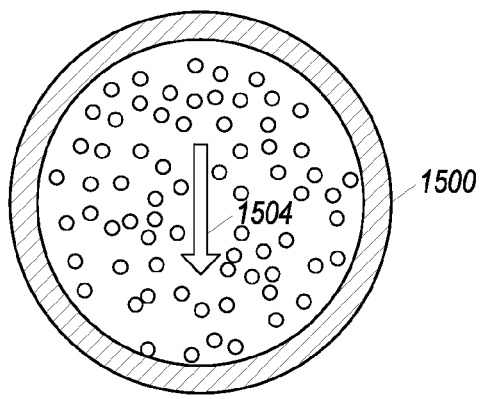
FIG. 15A-15F illustrate a cross section (perpendicular to a central axis) of a hollow fiber that may be part of a bioreactor as it progresses through steps of a process for distributing attaching and expanding cells in the bioreactor according to yet another embodiment.

Referring now to FIGS. 14A-14D and FIGS. 15A-15F these figures illustrate a cross-section of a hollow fiber 1400 (taken perpendicular to a central axis of the hollow fiber 1400 and a central axis of bioreactor 300) that may be one of the hollow fibers 316 of bioreactor 300. These figures illustrate the possible locations of cells within the hollow fibers 316 during some steps of flow chart 700. As illustrated in FIG. 14A, before the circulation rate is reduced at step 712, cells within individual hollow fiber 1400 may be distributed, in embodiments evenly, throughout the volume of hollow fiber 1400. When the circulation rate is reduced, the cells may begin to be influenced by gravity 1404 and begin to settle. FIG. 15A also illustrates a similar situation with respect to a hollow fiber 1500 and gravity 1504.

Figure 15B:
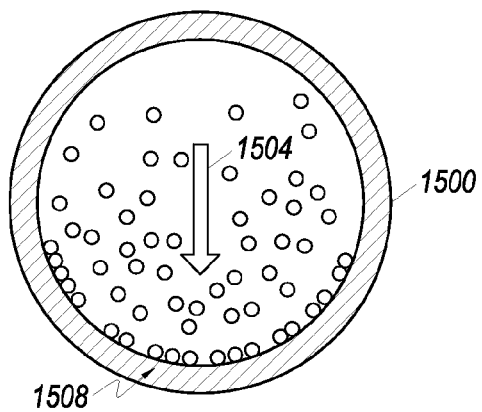

In embodiments, with the bioreactor 300 in the first horizontal orientation (FIG. 8), the cells within bioreactor 300 are allowed to settle onto a first portion of the bioreactor. As illustrated in FIGS. 14B and 15B, the first portion of bioreactor 300 may include at least a portion 1408 of hollow fiber 1400 and/or portion 1508 in hollow fiber 1500. In embodiments, the cells will be allowed to settle for a first predetermined period of time that may be selected to not only allow the cells to settle, but also to attach to portion 1408 of the hollow fiber 1400 (and 1508 of hollow fiber 1500).

In some embodiments, the first predetermined period of time may be long enough in duration to allow the cells to settle and attach to portion 1408 and 1508. In these embodiments, the cells may only need to travel the distance of the inner diameter of hollow fiber 1400 or 1500. For example, in embodiments where the hollow fiber has an inner diameter of between about 150 microns and about 300 microns, the first predetermined period of time may be less than about 20 minutes, less than about 15 minutes, or even less than about 10 minutes. In other embodiments, the first predetermined period of time may be greater than about 1 minute, greater than about 2 minutes, greater than about 3 minutes, or even greater than about 4 minutes. In one embodiment, the first period of time may be between about 3 minutes and about 8 minutes, such as about 5 minutes.

After step 720, flow passes to step 724, where the bioreactor 300 is rotated to a second horizontal orientation that is about 180 degrees from the first horizontal orientation. As shown in FIGS. 8-10, the bioreactor may be rotated by first being rotated from its first horizontal orientation (FIG. 8) to a first vertical orientation, which is about 90 degrees from the first horizontal orientation, e.g. axis LA LA in a vertical orientation (FIG. 9). Bioreactor 300 may then be rotated another 90 degrees (FIG. 10) to complete the rotation to the second horizontal orientation. Step 724 may in some embodiments be performed by one or more motors connected to bioreactor 300. These motors may be part of a rocking device.

Figure 15C:
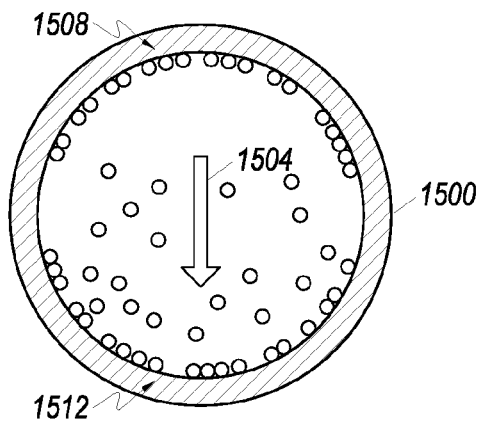
Figure 15D:
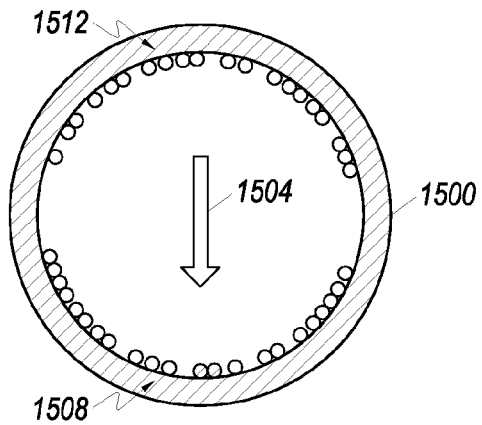
Figure 15E:
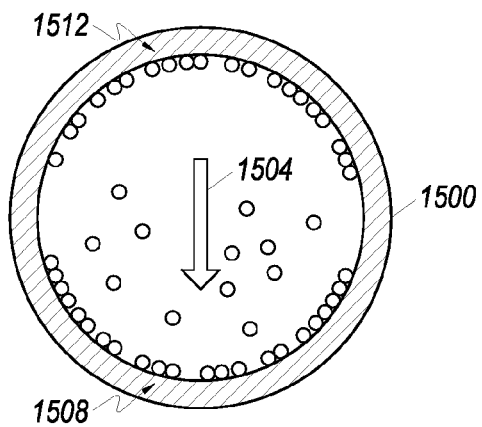

In some embodiments, flow 700 will pass from step 724 to step 736 where the bioreactor 300 is maintained in the second horizontal orientation (FIG. 10) for a second predetermined period of time so that the cells are allowed to settle to a second portion of the bioreactor, such as portion 1412 of hollow fiber 1400 (FIG. 14C) or portion 1512 of hollow fiber 1500 (FIG. 15C).

In some embodiments, flow 700 may include optional steps 728 and 732 prior to proceeding to step 736. Similar to step 708, step 728 provides for circulating fluid through the bioreactor 300. In embodiments, step 728 may involve activating one or more pumps to circulate fluid through the bioreactor 300. As noted above, an IC circulation pump (e.g., 812 or 911) may be activated to circulate fluid through the IC side of bioreactor 300 at a second circulation flow rate. In at least one embodiment, fluid carrying the cells may pass through hollow fibers of the bioreactor 300 from the IC side to the EC side. In other embodiments, cells may be loaded into the EC side of the bioreactor 300 and have the fluid carrying the cells pass from the EC side to the IC side. In these embodiments, an EC circulation pump (e.g., 828 or 974) may be activated to circulate fluid through the EC side of bioreactor 300 at a second circulation flow rate.

In embodiments, the second circulation flow rate may be less than the first circulation rate. In embodiments, the second circulation flow rate may be less than about 400 ml/min, less than about 300 ml/min, or even less than about 200 ml/min. In other embodiments, the second circulation rate may be greater than about 25 ml/min, greater than about 500 ml/min, or even greater than about 75 ml/min. In one embodiment, the second circulation flow rate is between about 50 ml/min and about 150 ml/min, such as about 100 ml/min.

In some embodiments, step 728 may also involve circulation in a different direction than the circulation performed in step 708. In other words, in some embodiments, step 708 may involve circulating fluid in a counter clockwise direction (see IC loop in FIGS. 8 and 9). In some embodiments, the circulation at step 728 may be clockwise. In other words, the circulation may flow opposite to the circulation at step 708. In other embodiments, the circulation in step 708 may flow in the same direction as step 708, clockwise or counter clockwise.

Optional step 728 may in some embodiments involve also rotating the bioreactor 300 in a particular sequence to facilitate distribution of the cells through the bioreactor 300 and circulation paths of the CES to which the bioreactor 300 may be fluidly associated. In other embodiments, the circulating step 728 may involve rotating the bioreactor 300 for some periods of time, but maintaining the bioreactor 300 stationary for other periods of time.

After optional step 728, the fluid circulation rate is once again reduced at step 732. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers 316 of bioreactor 300. In embodiments, step 732 may involve stopping or turning off one or more pumps used in step 728 to circulate the fluid.

Referring once again to step 736, maintaining the bioreactor in the second horizontal orientation allows cells to settle on portion 1412 (or 1512 in FIG. 15C), which may be opposite portion 1408, e.g., portion 1408 (or 1508) may be referred to as a "bottom portion" and portion 1412 (or 1512 in FIG. 15C) may be referred to as a "top portion." FIGS. 14C and 15C illustrate cells settling onto portions 1412 and 1512, or in some embodiments vice versa. In embodiments, the cells will be allowed to settle for a second predetermined period of time that may be selected to not only allow the cells to settle, but also to attach to portion 1412 of the hollow fiber 1400 (or 1512 of fiber 1500).

In some embodiments, the second predetermined period of time may be long enough in duration allow the cells to settle and attach to portion 1412 (or 1512 in FIG. 15C). In these embodiments, the cells may only need to travel the distance of the inner diameter of hollow fiber 1400 or 1500. For example, in embodiments where the hollow fiber has an inner diameter of between about 150 microns and about 300 microns, the second predetermined period of time may be less than about 20 minutes, less than about 15 minutes, or even less than about 10 minutes. In other embodiments, the second predetermined period of time may be greater than about 1 minute, greater than about 2 minutes, greater than about 3 minutes, or even greater than about 4 minutes. In one embodiment, the second period of time may be between about 3 minutes and about 8 minutes, such as about 5 minutes.

In some embodiments, after step 736, flow 700 may pass to step 772 where cells are expanded. Step 772 may involve a number of substeps, such as circulating fluid into the bioreactor to feed and provide nutrients to the cells attached in the bioreactor. As can be appreciated, step 772 may also involve providing oxygen to the cells so that they may multiply. Several other parameters in the bioreactor may be controlled in order to optimize the expansion, i.e. growth of the cells. In some embodiments, step 772 may include circulating fluid to feed the cells for about 24 hours, about 36 hours, about 48 hours, about 60 hours, or even about 72 hours. In some embodiments, the feeding of the cells as part of step 772 may be performed for less than about 120 hours, less than about 108 hours, less than about 96 hours, less than about 84 hours, or even less than about 72 hours. FIG. 14D illustrates hollow fiber 1400 for this embodiment. Flow then ends at 776.

In other embodiments, flow 700 may pass to step 740, where the bioreactor 300 is rotated back to its original first horizontal orientation. FIG. 11 illustrates bioreactor 300 once it has been rotated back to its first horizontal orientation. Step 740 may be performed by one or more motors connected to bioreactor 300. These motors may be part of a rocking device. In embodiments, flow may pass from step 740 to step 772 where the cells are expanded. Flow then ends at 776.

In other embodiments, flow 700 passes from step 740 to step 744, or in other embodiments, flow may pass directly from step 736, to step 744 (when no additional rotation is performed), where fluid is again circulated but at a third circulation flow rate. Similar to steps 708 and 728, fluid is circulated through the bioreactor 300. In embodiments, step 744 may involve activating one or more pumps to circulate fluid through the bioreactor 300. As noted above, an IC circulation pump (e.g., 812 or 911) may be activated to circulate fluid through the IC side of bioreactor 300 at a third circulation flow rate. In at least one embodiment, fluid carrying the cells may pass through hollow fibers of the bioreactor 300 from the IC side to the EC side. In other embodiments, cells may be loaded into the EC side of the bioreactor 300 and have the fluid carrying the cells pass from the EC side to the IC side. In these embodiments, an EC circulation pump (e.g., 828 or 974) may be activated to circulate fluid through the EC side of bioreactor 300 at the third circulation flow rate.

In embodiments, the third circulation flow rate may be less than the second circulation rate. In embodiments, the third circulation flow rate may be less than about 200 ml/min, less than about 150 ml/min, or even less than about 100 ml/min. In other embodiments, the third circulation rate may be greater than about 10 ml/min, greater than about 20 ml/min, or even greater than about 30 ml/min. In one embodiment, the third circulation flow rate is between about 20 ml/min and about 100 ml/min, such as about 50 ml/min.

In some embodiments, step 744 may also involve circulation in a different direction than the circulation performed in step 728. In other words, in some embodiments, step 728 may involve circulating fluid in a clockwise direction. In some embodiments, the circulation at step 744 may be similar to step 708 and be in a counter clockwise direction (see IC loop in FIGS. 8 and 9). In other words, the circulation at step 744 may flow opposite to the circulation at step 728, and the same as the direction of circulation of step 708. In other embodiments, the circulation in steps 708, 728, 744 may flow in the same direction, clockwise or counter clockwise.

Optional step 744 may in some embodiments involve also rotating the bioreactor 300 in a particular sequence to facilitate distribution of the cells through the bioreactor 300 and circulation paths of the CES to which the bioreactor 300 may be fluidly associated. In other embodiments, the circulating step 744 may involve rotating the bioreactor 300 for some periods of time, but maintaining the bioreactor 300 stationary for other periods of time.

Flow passes from 744 to step 748, where, the fluid circulation rate is once again reduced. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers 316 of bioreactor 300. In embodiments, step 748 may involve stopping or turning off one or more pumps used in step 744 to circulate the fluid.

From step 748, flow passes to step 752 where the bioreactor is maintained in a horizontal orientation. In those embodiments that include step 744 (rotate to first orientation), step 752 will involve maintaining the first horizontal orientation. In those embodiments that do not include the rotation of step 740, step 752 will involve maintaining the second horizontal orientation. In any case, step 752 is performed to allow cells to settle again, such as on portion 1508 (See FIGS. 15D and 15E; if the rotation step 740 is performed). In embodiments, the cells will be allowed to settle for a third predetermined period of time that may be selected to not only allow the cells to settle, but also to attach.

In some embodiments, the third predetermined period of time may be long enough in duration to allow the cells to settle and attach to portion 1508. In these embodiments, the cells may only need to travel the distance of the inner diameter of hollow fiber 1500. For example, in embodiments where the hollow fiber 1500 has an inner diameter of between about 150 microns and about 300 microns, the third predetermined period of time may be less than about 20 minutes, less than about 15 minutes, or even less than about 10 minutes. In other embodiments, the third predetermined period of time may be greater than about 1 minute, greater than about 2 minutes, greater than about 3 minutes, or even greater than about 4 minutes. In one embodiment, the third period of time may be between about 3 minutes and about 8 minutes, such as about 5 minutes.

Figure 15F:
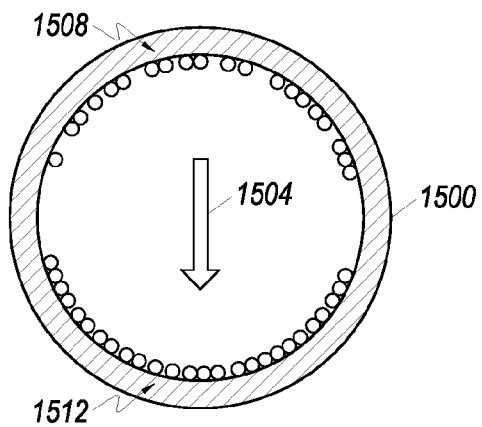

In some embodiments, flow 700 may pass from step 752 to step 772 where the cells are expanded. FIG. 15F illustrates fiber 1500 in these embodiments. Flow would then end at 776.

In other embodiments, as described below, flow 700 may include additional rotation (756), circulation (760), reduce circulation (764), and maintain orientation (768) steps before moving to step 772 where cells are expanded. In these embodiments, flow 700 may pass from step 752 to step 756, where the bioreactor 300 is rotated back to the second horizontal orientation, if it was rotated at step 740 to the first horizontal orientation. FIG. 10 illustrates bioreactor 300 in the second horizontal orientation. Step 756 may be performed by one or more motors connected to bioreactor 300. These motors may be part of a rocking device. In some embodiments, this step may be unnecessary, if step 740 was not performed to rotate the bioreactor to the first horizontal orientation.

Flow 700 passes to step 760 where fluid is again circulated but at a fourth circulation flow rate. Similar to steps 708, 728, and 744, fluid is circulated through the bioreactor 300. In embodiments, step 744 may involve activating one or more pumps to circulate fluid through the bioreactor 300, as noted above, an IC circulation pump (e.g., 812 or 911) may be activated to circulate fluid through the IC side of bioreactor 300 at a fourth circulation flow rate. In at least one embodiment, fluid carrying the cells may pass through hollow fibers of the bioreactor 300 from the IC side to the EC side. In other embodiments, cells may be loaded into the EC side of the bioreactor 300 and have the fluid carrying the cells pass from the EC side to the IC side. In these embodiments, an EC circulation pump (e.g., 828 or 974) may be activated to circulate fluid through the EC side of bioreactor 300 at the fourth circulation flow rate.

In embodiments, the fourth circulation flow rate may be less than the third circulation rate. In embodiments, the fourth circulation flow rate may be less than about 100 ml/min, less than about 75 ml/min, or even less than about 50 ml/min. In other embodiments, the fourth circulation rate may be greater than about 5 ml/min, greater than about 10 ml/min, or even greater than about 15 ml/min. In one embodiment, the fourth circulation flow rate is between about 15 ml/min and about 35 ml/min, such as about 25 ml/min.

In some embodiments, step 760 may also involve circulation in a different direction than the circulation performed in step 744. In other words, in some embodiments, step 744 may involve circulating fluid in a counter clockwise direction. In some embodiments, the circulation at step 760 may be similar to step 728 and be in a clockwise direction. In other words, the circulation at step 760 may flow opposite to the circulation at step 744, and the same as the direction of circulation of step 728. In other embodiments, the circulation in steps 708, 728, 744 and 760 may flow in the same direction, clockwise or counter clockwise.

Step 760 may in some embodiments involve also rotating the bioreactor 300 in a particular sequence to facilitate distribution of the cells through the bioreactor 300 and circulation paths of the CES to which the bioreactor 300 may be fluidly associated. In other embodiments, the circulating step 760 may involve rotating the bioreactor 300 for some periods of time, but maintaining the bioreactor 300 stationary for other periods of time.

Flow passes from 760 to step 764, where, the fluid circulation rate is once again reduced. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers 316 of bioreactor 300. In embodiments, step 764 may involve stopping or turning off one or more pumps used in step 760 to circulate the fluid.

From step 764, flow passes to step 768 where the bioreactor is maintained in the second horizontal orientation to allow cells to settle on for example portion 1512 again (see FIG. 15F). In embodiments, the cells will be allowed to settle for a fourth predetermined period of time that may be selected to not only allow the cells to settle, but also to attach once again.

In some embodiments, the fourth predetermined period of time may be long enough in duration allow the cells to settle and attach. In these embodiments, the cells may only need to travel the distance of the inner diameter of the hollow fiber, e.g., fiber 1500. For example, in embodiments where the hollow fiber 1500 has an inner diameter of between about 150 microns and about 300 microns, the fourth predetermined period of time may be less than about 20 minutes, less than about 15 minutes, or even less than about 10 minutes. In other embodiments, the fourth predetermined period of time may be greater than about 1 minute, greater than about 2 minutes, greater than about 3 minutes, or even greater than about 4 minutes. In one embodiment, the fourth period of time may be between about 3 minutes and about 8 minutes, such as about 5 minutes.

After step 768, flow 700 passes to step 772 where the cells settled and attached to the bioreactor 300, e.g., to hollow fibers of the bioreactor, are expanded, i.e., multiplied. Flow 700 then ends at 776.

Without being bound by theory, it is believe that in embodiments, the cell expansion is improved if the steps of flow 700 are performed. It is believed that these embodiments help to ensure that more portions of the bioreactor, e.g., surface of hollow fibers in the bioreactor, are seeded with cells prior to cell expansion. This may provide for more cells to initially be seeded, and ultimately may improve cell yield and reduce cell doubling time, as compared to conventional processes.

Although flow 700 includes specific number of steps that provide for rotating, circulating, reducing circulation, and maintaining the orientation of the bioreactor, other embodiments are not limited to these specific number of steps. In other embodiments, even after step 768, the bioreactor may be rotated again, circulation can be restarted again, followed by another period of reducing circulation to allow cells to settle and maintain the orientation for a period of time to allow cells to attach to portion of a bioreactor. These steps may be performed any number of times. In embodiments, each time the circulation is restarted, it is at a lower rate than the previous circulation. In other embodiments, the circulation rates may be the same each time circulation is started. In yet other embodiments, the direction of circulation may be changed, with circulation in a first direction, followed by stopping the circulation to allow the cells to settle and attach, circulation in a direction opposite the first direction (clockwise vs. counter clockwise) and again stopping the circulation to allow the cells to settle.

Figure 16:
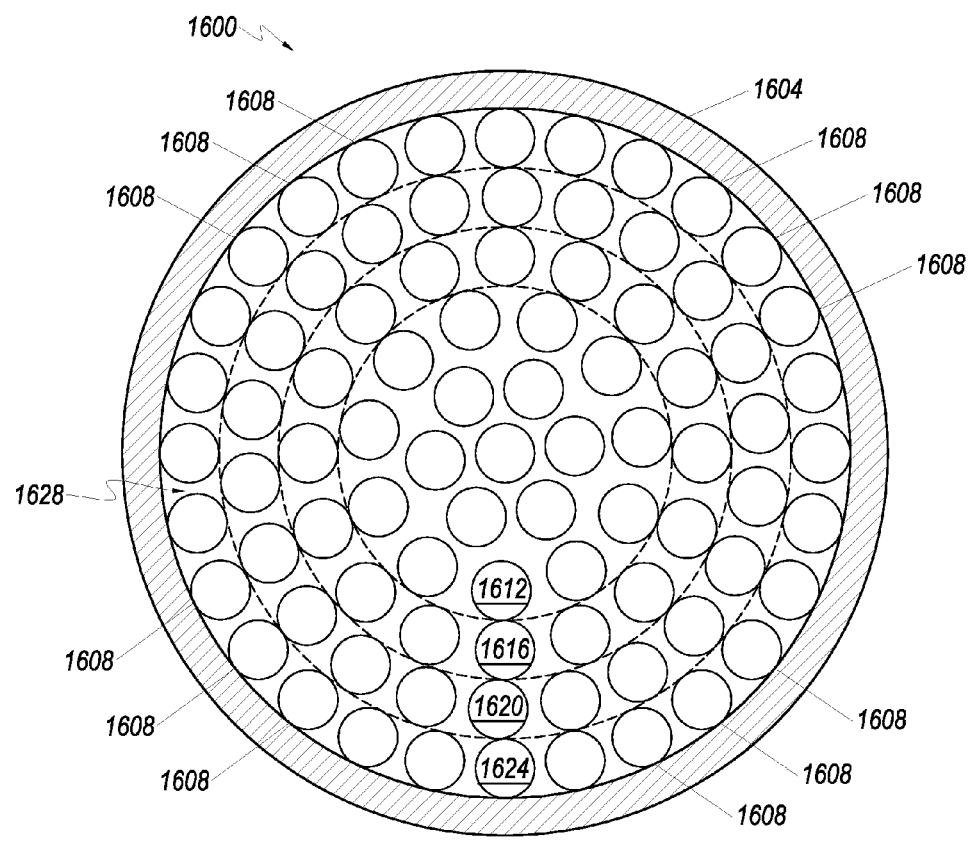
FIG. 16 illustrates a cross section of a bioreactor showing a plurality of hollow fibers and zones of hollow fibers through which liquid containing cells may circulate at different flow rates.

Referring now to FIG. 16, a cross section 1600 (perpendicular to a central axis) of a bioreactor (e.g., bioreactor 300) is shown. The cross section 1600 illustrates a plurality of hollow fibers 1608 which may be within a housing 1604. The cross section 1600 is taken from one end of a bioreactor and illustrates, in addition to the hollow fibers 1608 a matrix material 1628 (which may be referred to above as potting material) that holds the hollow fibers 1608 together.

Also shown in FIG. 16 are zones 1612, 1616, 1620 and 1624. These zones represent fibers that may have fluid circulating through them at different flow rates. In other words, without being bound by theory, it is believed that circulation at relatively high flow rates, such as rates that may be used in circulation steps 708 or 728 (FIG. 7) may primarily flow through fibers in zone 1612. Without being bound by theory, it is believed that the higher flow rates do not allow fluid to disperse enough to flow evenly into the hollow fibers in the outer zones. As the flow rate is reduced, such as in steps 744 and 760, it is believed that the fluid may disperse into hollow fibers in outer zones, such as 1616, 1620 and 1624.

Accordingly, without being bound by theory, it is believed that having steps 708, 728, 744 and 752 circulate at different flow rates, allows the fluid to flow through more of the hollow fibers 1608 than if just a single flow rate would be used. In one embodiment of a process that follows flow chart 700, at step 708 (at the flow rates described above), fluid may flow through the hollow fibers in zone 1612. At step 728 (at the flow rates described above), fluid may flow through the hollow fibers in both zones 1612 and 1616 because the rate is slower and the fluid may disperse more. At step 744 (at the flow rates described above), fluid may flow through the hollow fibers in zones 1612, 1616, and 1620 because the flow rate is yet slower and fluid may disperse even more. At step 752 (at the flow rates described above), fluid may flow through the hollow fibers in all the zones 1612, 1616, 1620 and 1624 because the flow rates are even slower and the fluid may disperse through all of the fibers in the various zones. Thus, it is believe that fluid with the cells may flow into more of the hollow fibers using a sequence of different flow rates, than if a single high flow rate circulation is used.

Furthermore, it is also believed that the different flow rates may also affect the longitudinal distribution of cells along the bioreactor, e.g., along a hollow fiber. That is, a higher flow rate may allow cells to flow further along inside a hollow fiber. For example, at a higher flow rate, a cell being carried by fluid may reach beyond half the length of the hollow fiber. At a lower flow rate, a cell being carried by fluid may reach half the length of the hollow fiber. At even a lower flow rate, a cell being carried by fluid may reach less than half the length of the hollow fiber. Accordingly, in some embodiments, it is believed that the use of different flow rates may provide some improvement in longitudinal distribution of cells along the length of the bioreactor, e.g., a hollow fiber.

It is noted that the embodiments described with respect to flow charts 500, 600 and 700 may be used in the expansion of any type of cell some non-limiting examples including, stem cells (mesenchymal, hematopoietic, etc.), fibroblasts, keratinocytes, progenitor cells, endothelial cells, other fully differentiated cells and combinations thereof. Different cells may be expanded using processes that have different features, and combinations of features, some of which may include steps described above with respect to flow charts 500, 600 and/or 700.

Although flow charts 500 (FIG. 5), 600 (FIG. 6) and 700 (FIG. 7) have been described with steps listed in a particular order, the present invention is not limited thereto. In other embodiments, steps may be performed in different order, in parallel, or any different number of times, e.g., before and after another step. Also, as indicated above, flow charts 500, 600 and 700 may include some optional steps or sub-steps. However, those steps above that are not indicated as optional should not be considered as essential to the invention, but may be performed in some embodiments of the present invention and not in others.

Figure 17:
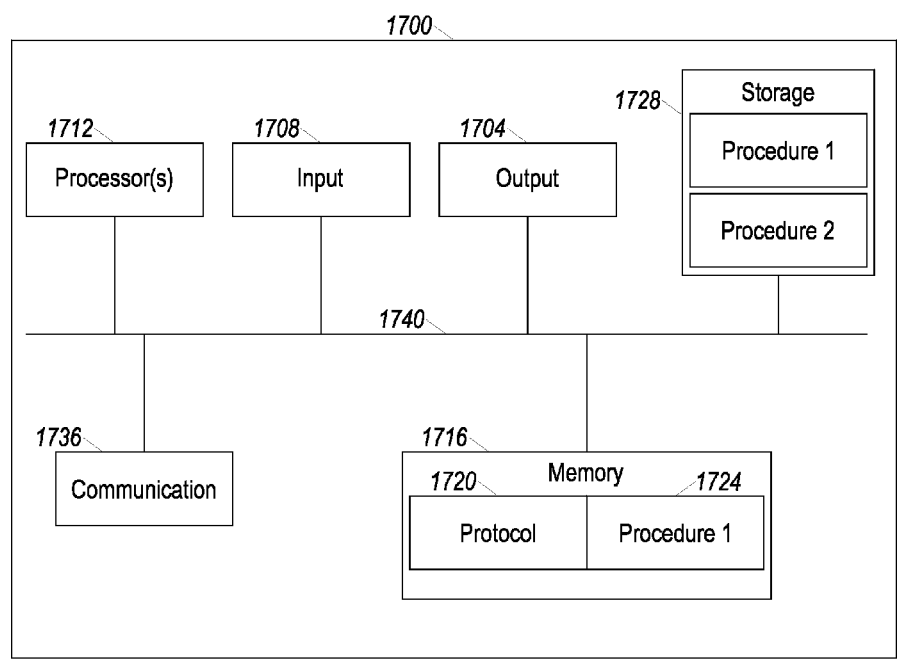
FIG. 17 illustrates a block diagram of a basic computer that may be used to implement embodiments.

Finally, FIG. 17 illustrates example components of a basic computer system 1700 upon which embodiments of the present invention may be implemented. Computer system 1700 may perform some steps in the methods for loading and distributing cells. System 1700 may be a controller for controlling features, e.g., flow control devices, pumps, valves, rotation of bioreactors, motors, etc., of CES systems 10, 430, 800, and 900 shown above in which cells are loaded and distributed for expansion.

Computer system 1700 includes output device(s) 1704, and/or input device(s) 1708. Output device(s) 1704 may include one or more displays, including CRT, LCD, and/or plasma displays. Output device(s) 1704 may also include a printer, speaker, etc. Input device(s) 1708 may include a keyboard, touch input devices, a mouse, voice input device, etc.

Basic computer system 1700 may also include a processing unit 1712 and/or a memory 1716, according to embodiments of the present invention. The processing unit 1712 may be a general purpose processor operable to execute instructions stored in memory 1716. Processing unit 1712 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits.

The memory 1716 may include any tangible medium for short-term or long-term storage for data and/or processor executable instructions, according to embodiments. The memory 1716 may include, for example, Random Access Memory (RAM), Read-Only Memory (ROM), or Electrically Erasable Programmable Read-Only Memory (EEPROM). Other storage media may include, for example, CD-ROM, tape, digital versatile disks (DVD) or other optical storage, tape, magnetic disk storage, magnetic tape, other magnetic storage devices, etc. In embodiments, system 1700 may be used to control the rotation of bioreactor 300 and/or various flow control devices, pumps, valves, etc. of CES systems. Memory 1716 can store protocols 1720 and procedures 1724, such as protocols and procedures for loading and distributing cells in a bioreactor, which would control operation of circulation pumps, valves, rotation of bioreactor(s), etc.

Storage 1728 may be any long-term data storage device or component. Storage 1220 may include one or more of the systems described in conjunction with memory 1716, according to embodiments. Storage 1728 may be permanent or removable. In embodiments, system 1700 is part of a CES system and storage 1728 may store various procedures for utilizing a CES system to load, distribute, attach, expand, and harvest cells of various types.

EXAMPLES

Below, some examples of specific embodiments of the present invention are described. However, it is noted that although specific parameters, features, and/or values are described below, e.g., for programming a CES (namely a QUANTUM® cell expansion system), according to some embodiments, these are provided merely for illustrative purposes, and the present invention is not limited to the specific details provided below.

Example 1

The objective of this study is to characterize the expansion of human bone marrow derived mesenchymal stem cells (hMSCs) using two unique cell seeding methodologies in the QUANTUM® cell expansion system.

The current cell loading procedure used on the QUANTUM cell expansion system for pre-selected hMSCs distributes the cells in the bioreactor via uniform cell suspension. The cells are loaded into the IC Circulation loop of the QUANTUM cell expansion system and then circulated at relatively high flow rates (200 mL/min) for two minutes. This circulation method, coinciding with deliberate bioreactor motion, results in a uniform suspension of cells. Once the cells are uniformly suspended, circulation and bioreactor motion stops and the cells settle onto the bioreactor surface.

One limitation of this cell loading procedure is that only the trough of the bioreactor fiber is seeded with cells. hMSCs are frequently seeded at a specified cell density (e.g., 500 cells/cm$^2$). In order to achieve a specified seed density, only approximately 50% of the bioreactor surface area can be considered when determining the appropriate number of cells to load. At 500 cells/cm$^2$, the QUANTUM cell expansion system bioreactor can be seeded with 10.5E+06 cells (500 cells/cm$^2$×21000 cm$^2$). However, only 50% of the bioreactor surface area can be considered "seed able" due to the aforementioned mechanics of the current cell load protocol. In addition, expanding cells attempting to migrate to the "unseedable" surface of the bioreactor must overcome gravity in order to utilize that surface. It is theorized here that migrating cells may take the path of least resistance; resulting in rapid confluence within the cell population compared to those expanded in its flask counter-part.

A total of seven sterilized Quantum CES Disposable sets with a bioreactor may be fibronectin coated (5 mg) overnight. All Quantum systems may be seeded with pre-cultured hMSCs. One Quantum cell expansion system may use the current Load with Circulation Task and serve as the experiment control. Three Quantum cell expansion systems may use "Load with Circulation Task: Modification 1" (Modification 1) and three Quantum cell expansion systems may use "Load with Circulation Task: Modification 2" (Modification 2).

Disposable Sets: All bioreactors may be integrated into a QUANTUM cell expansion system (CES) disposable set and sterilized with ethylene oxide.

Cell Source and Density: The bioreactor that may be used may have a 2.1 m$^2$ inner (IC) surface area. As a result, an adjustment to seeding densities for control flasks may need to be made based on the bioreactor volume fraction of the IC loop. All bioreactors may be uniformly loaded with a maximum of 20E+06 pre-selected MSCs (existing passages 1-3) from a direct re-load of the same cell source. Cells from a single donor are preferred. Seed three (3) T25 control flasks with hMSCs at the same density per cm$^2$ as the bioreactor for comparative purposes.

CES Media IC Input Q Management & Harvest: The media feed rate (IC Input Q) may be doubled when the glucose levels fall below 70 mg/dL; the IC Input Q may be doubled a second time in the course of one day if the glucose values continue to fall below 70 mg/dL. All disposable sets may be harvested at the same time and no later than Day 8 to limit potential aggregation. Cell harvest time may be determined as a result of the metabolic characteristics displayed by the cell cultures. The target harvest time may be post-log phase growth of the cells.

Post-Harvest Evaluation: Evaluations may be performed on each of the harvest products. These evaluations may include cell count and viability.

Quantum CES Cell Load Modification 1

The current cell load procedure may be performed with the following modifications shown in bold. After allowing the cells to attach for 5 minutes, all bioreactors may be rotated 180 degrees to allow unattached cells to settle to the top of the hollow fiber membrane for an additional 5 minutes. Then bioreactor may be rotated back to the home horizontal position and proceed with the expansion protocol. The rationale for the modification is to distribute the cells over the entire surface area of the bioreactor hollow fiber.

Day: 0 Attach Cells with One (1) Rotation

Purpose: enables adherent cells to attach to the bioreactor membrane while allowing flow on the EC circulation loop. The pump flow rate to the IC loop may be set to zero.

Table 1 describes the bags of solution that may be attached to each line when performing Attach Cells. These solutions and corresponding volumes are based on the default settings for this task.

Table 1: Solutions for Attach Cells Modification 1

TABLE 1

Solutions for Attach Cells
Table 1: Solutions for Attach Cells

| Bag | Solution in Bag | Volume (estimate based on factory default) |
|---|---|---|
| Cell Inlet | None | N/A |
| Reagent | None | N/A |
| IC Media | Media with Protein | 6 mL/hour |
| Wash | None | N/A |
| EC Media | None | N/A |

Cells Pathway: Task>Load and Attach>Attach Cells

Enter the values for each setting for Attach Cells shown in Protocol Table 2 a-c.

TABLE 2a

Task > Load and Attach > Attach Cells, Step 1 Modification 1
Table 2a: Task Settings for Attach Cells, Step 1

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | [EC Media] | IC Media | |
| EC Inlet Rate | 0 | | |
| EC Circulation Rate | 0 | | |
| Outlet | EC Waste | | |
| Rocker Control | [Stationary (0°)] | | Stationary 180° |
| Stop Condition | [Manual] | | Time: 5 minutes |

TABLE 2b

Task > Load and Attach > Attach Cells, Step 2 Modification 1
Table 2b: Task Settings for Attach Cells, Step 2

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | [EC Media] | IC Media | |
| EC Inlet Rate | 0 | | |
| EC Circulation Rate | 0 | | |
| Outlet | EC Waste | | |
| Rocker Control | Stationary (0°) | | |
| Stop Condition | [Manual] | | Time: 5 minutes |

TABLE 2c

Task > Load and Attach > Attach Cells, Step 3 Modification 1
Table 2c: Task Settings for Attach Cells, Step 3

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | [EC Media] | IC Media | |
| EC Inlet Rate | 0.1 | | |
| EC Circulation Rate | 30 | | |
| Outlet | EC Waste | | |
| Rocker Control | [Stationary (0°)] | | Stationary 180° |
| Stop Condition | Manual | | |

Quantum CES Cell Load Modification 2

The current cell load procedure, pre-selected MSC Expansion Protocol, may be performed with the following modifications shown in bold. Cells may be attached to the top of the hollow fiber by rotating the bioreactor to the 180 degree position during the cell attachment phase (18-24 hours). Then rotate the bioreactor back to the home position and proceed with the expansion protocol. The rationale for the modification is to allow gravity to influence the direction of cell migration toward the empty growth surface during cell expansion.

The force of gravity may be used to "influence" the cell migration during expansion. This may be accomplished by seeding the cells as described in the current cell load procedure, then during expansion the bioreactor may be rotated 180°. In this configuration the unoccupied growth surface of the bioreactor is below the seeded cells. The cells may then expand in the direction of least resistance (e.g., downward, aided by gravity).

Day: 0 Attach Cells with One (1) Rotation

Purpose: enables adherent cells to attach to the bioreactor membrane while allowing flow on the EC circulation loop. The pump flow rate to the IC loop may be set to zero.

Table 5 describes the bags of solution that may be attached to each line when performing Attach Cells. These solutions and corresponding volumes are based on the default settings for this task.

TABLE 5

Solutions for Attach Cells Modification 2
Table 5: Solutions for Attach Cells

| Bag | Solution in Bag | Volume (estimate based on factory default) |
|---|---|---|
| Cell Inlet | None | N/A |
| Reagent | None | N/A |
| IC Media | Media with Protein | 6 mL/hour |
| Wash | None | N/A |
| EC Media | None | N/A |

Cells Pathway: Task>Load and Attach>Attach Cells

TABLE 6

Task > Load and Attach > Attach Cells Modification 2
Table 6: Task Settings for Attach Cells, Step 1

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | [EC Media] | IC Media | |
| EC Inlet Rate | 0.1 | | |
| EC Circulation Rate | 30 | | |
| Outlet | EC Waste | | |
| Rocker Control | [Stationary (0°)] | | Stationary 180° |
| Stop Condition | Manual | | |

The results may be as follows:

TABLE 7

| Quantum Run | Modification | hMSC Seeding | hMSC Seeding/$cm^2$ | Harvest hMSC | Harvest hMSC/$cm^2$ | Percent Increase |
|---|---|---|---|---|---|---|
| Q621 | Control | 1.05E+07 | 500 | 2.56E+08 | 12,194 | 0% |
| Q622 | Mod 1 | 1.05E+07 | 500 | 3.02E+08 | 14,376 | 18% |
| Q623 | Mod 1 | 1.05E+07 | 500 | 3.70E+08 | 17,620 | 36% |
| Q624 | Mod 1 | 1.05E+07 | 500 | 3.49E+08 | 16,596 | 51% |

TABLE 8

| Quantum Run | Modification | hMSC Seeding | hMSC Seeding//cm$^2$ | Harvest hMSC | Harvest hMSC/cm$^2$ | Percent Increase |
|---|---|---|---|---|---|---|
| | Control | 1.05E+07 | 500 | 2.56E+08 | 12,194 | 0% |
| Average | Mod 1 | 1.05E+07 | 500 | 3.40E+08 | 16,197 | 35% |

TABLE 9

| Load Condition | # of Cells Seeded | # Cells Harvested | Doubling Time (hrs) |
|---|---|---|---|
| Control | 10.5 × 10$^6$ | 256 × 10$^6$ | 34.9 |
| Gravity Influenced Expansion (Modification 2) | 10.5 × 10$^6$ | 345 × 10$^6$ | 30.9 |
| Gravity Influenced Expansion (Modification 2) | 10.5 × 10$^6$ | 347 × 10$^6$ | 31.9 |
| Gravity Influenced Expansion (Modification 2) | 10.5 × 10$^6$ | 388 × 10$^6$ | 31.9 |

Example 2

The Bull's Eye cell loading procedure is a series of steps designed to increase cell yield by allowing for a more even distribution of cells within the bioreactor of the QUANTUM® cell expansion system and by reducing the number of cells lost during a seeding process.

The Bull's Eye cell loading technique for the QUANTUM cell expansion system provides a series of steps that include and add to the 'Load Cells with Uniform Suspension' protocol (Quantum Cell Expansion System Operator's Manual for Software Version 2.0) that is commonly used to seed the bioreactor. In Load Cells with Uniform Suspension (LCWUS), suspended cells have a single opportunity to enter and attach to the internal surface of one fiber of the bioreactor after the cell suspension is circulated through the IC loop at 200 mL/min. Bull's Eye may allow cells that do not attach after the initial suspension and those that may be left in the IC loop rather than in the bioreactor to be re-suspended and transported to a different fiber within the bioreactor for subsequent attachment.

The Bull's Eye load may operate on the principle that a cell suspension introduced to the bioreactor via circulation of the IC loop may pass through a different set of bioreactor fibers depending on the rate of circulation of that cell suspension in the IC loop.

Following an initial 200 mL/min suspension cycle in loading cells with uniform suspension (LCWUS), the cell suspension in the IC loop may be circulated alternately in the positive and negative directions at sequentially lower circulation rates: –100 mL/min, 50 mL/min, –25 mL/min. Each progressively slower cycle of the IC loop may allow those cells still left in suspension an additional opportunity to enter and attach to the inner surface of a bioreactor fiber.

Each cycling of the fluid in the IC loop may be followed by a 7-minute cell-attachment period during which the IC circulation rate may be zero. MSC cells have been demonstrated to attach within 5 minutes to the inner surface of a fiber in a bioreactor used in the QUANTUM cell expansion system. As such, the 7-minute attachment may allow for 5 minutes for cell attachment, and 2 extra minutes to allow for slower-attaching cells. The four total cycles of cell suspension and cell attachment in the IC loop may be followed by a 24 hr attachment period after which an appropriate cell feeding schedule may be input as desired.

Day: –1 Coat Bioreactor
Purpose: coats the bioreactor membrane with a reagent.
Step 1: loads a reagent into the IC loop until the bag is empty.
Step 2: chases the reagent from the ARC into the IC loop.
Step 3: circulates the reagent in the IC loop.
Before starting this task, the following preconditions may be satisfied:
Include at least 40 mL of air in the cell inlet bag.
Table 10 describes the bags of solution that may be used to attach to each line when performing Coat Bioreactor. These solutions and corresponding volumes may be based on the default settings for this task.

TABLE 10

Solutions for Coat Bioreactor

| Bag | Solution in Bag | Volume (estimation based on factory default values) |
|---|---|---|
| Cell Inlet | None | N/A |
| Reagent | Fibronectin | 5 mg Fibronectin in 100 mL PBS |
| IC Media | None | N/A |
| Wash | PBS | 0.1 L + 6 mL/hr (overnight) |
| EC Media | None | N/A |

Coat Bioreactor Pathway: Task>System Management>Coat Bioreactor
Enter the values for each setting for step 1 shown in Table 11.

TABLE 11

Step 1 for Coat Bioreactor

| Setting | Factory Default | Laboratory Default | Modifications |
|---|---|---|---|
| IC Inlet | Reagent | | |
| IC Inlet Rate | 10 mL/min | | |
| IC Circulation Rate | 100 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | Stationary (0°) | | |
| Stop Condition | Empty Bag | | |

Enter the values for each setting for step 2 shown in Table 12.

TABLE 12

Step 2 Setting for Coat Bioreactor

| Setting | Factory Default | Laboratory Default | Modifications |
|---|---|---|---|
| IC Inlet | Wash | | |
| IC Inlet Rate | 10 mL/min | | |
| IC Circulation Rate | 100 mL/min | | |
| EC Inlet | None | | |

TABLE 12-continued

Step 2 Setting for Coat Bioreactor

| Setting | Factory Default | Laboratory Default | Modifications |
|---|---|---|---|
| EC Inlet Rate | 0 mL/min | | |
| EC Circulation Rate | 30 mL/min | | |
| Outlet | EC Outlet | | |
| Rocker Control | Stationary (0°) | | |
| Stop Condition | IC Volume (22 mL) | | |

Enter the values for each setting for step 3 shown in Table 13.

TABLE 13

Step 3 Settings for Coat Bioreactor

| Setting | Factory Default | Laboratory Default | Modifications |
|---|---|---|---|
| IC Inlet | None | | |
| IC Inlet Rate | 0 mL/min | | |
| IC Circulation Rate | 20 mL/min | | |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Manual | | |

Day: 0 IC EC Washout

Purpose: used to replace the fluid on both the IC circulation loop and the EC circulation loop. The replacement volume is specified by the number of IC Volumes and EC Volumes exchanged. Table 14 describes the bags of solution that may be attached to each line when performing IC EC Washout. These solutions and corresponding volumes may be based on the default settings for this task.

TABLE 14

Solutions for IC EC Washout

| Bag | Solution in Bag | Volume (estimation based on factory default values) |
|---|---|---|
| Cell Inlet | None | N/A |
| Reagent | None | N/A |
| IC Media | Media with Protein | 1.4 L |
| Wash | None | N/A |
| EC Media | None | N/A |

IC EC Washout Pathway: Task>Washout>IC EC Washout

Confirm the values for each setting for IC EC Washout shown in Table 15.

TABLE 15

Task Settings for IC EC Washout

| Setting | Factory Default | Laboratory Default | Modifications |
|---|---|---|---|
| IC Inlet | IC Media | | |
| IC Inlet Rate | 100 mL/min | | |
| IC Circulation Rate | −17 mL/min | | |
| EC Inlet | [EC Media] | IC Media | |
| EC Inlet Rate | 148 mL/min | | |
| EC Circulation Rate | −1.7 mL/min | | |
| Outlet | IC and EC Outlet | | |

TABLE 15-continued

Task Settings for IC EC Washout

| Setting | Factory Default | Laboratory Default | Modifications |
|---|---|---|---|
| Rocker Control | In Motion (−90°, 180°, 1 sec) | | |
| Stop Condition | Exchange (2.5 IC Volumes) (2.5 EC Volumes) | | |

Day: 0 Condition Media

Follow the instructions in this task to allow the media to reach equilibrium with the provided gas supply before loading the cells. This task may include two separate steps:

Step 1: provides rapid contact between the media and the gas supply by using a high EC circulation rate.

Step 2: maintains the system in a proper state until the operator is ready to load the cells.

Table 16 describes the bags of solution that may be attached to each line when performing Condition Media. These solutions and corresponding volumes may be based on the default settings for this task.

TABLE 16

Solutions for Condition Media

| Line | Solution in Bag | Volume (estimation based on factory default values) |
|---|---|---|
| Cell Inlet | None | N/A |
| Reagent | None | N/A |
| IC Media | None | N/A |
| Wash | None | N/A |
| EC Media | Media without Protein | 0.1 L plus 6 mL/hour |

Condition Media Pathway: Task>System Management>Condition Media

Enter the values for each setting for step 1 shown in Table 17.

TABLE 17

Step 1 Settings for Condition Media

| Setting | Factory Default | Laboratory Default | Modifications |
|---|---|---|---|
| IC Inlet | None | | |
| IC Inlet Rate | 0 mL/min | | |
| IC Circulation Rate | 100 mL/min | | |
| EC Inlet | [EC Media] | IC Media | |
| EC Inlet Rate | 0.1 mL/min | | |
| EC Circulation Rate | 250 mL/min | | |
| Outlet | EC Outlet | | |
| Rocker Control | Stationary (0°) | | |
| Stop Condition | Time (10 min) | | |

Enter the values for each setting for step 2 shown in Table 18.

TABLE 18

Step 2 Settings for Condition Media

| Setting | Factory Default | Laboratory Default | Modifications |
|---|---|---|---|
| IC Inlet | None | | |
| IC Inlet Rate | 0 mL/min | | |
| IC Circulation Rate | 100 mL/min | | |

TABLE 18-continued

Step 2 Settings for Condition Media

| Setting | Factory Default | Laboratory Default | Modifications |
|---|---|---|---|
| EC Inlet | [EC Media] | IC Media | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Manual | | |

Day: 0 Load Cells with Uniform Suspension

Purpose: loads the cells into the bioreactor from the cell inlet bag until the bag is empty. This task only uses IC circulation to distribute the cells and does not attempt to chase the cells from the line into the bioreactor. This task may include three separate steps.

Step 1: loads the cells from the cell inlet bag into the bioreactor.

Step 2: chases the cells from the ARC to the bioreactor. Larger chase volumes spread the cells and move them towards the IC outlet.

Step 3: promotes distribution of cells across membrane via IC circulation and no IC inlet thus no ultrafiltration.

Before starting this task, the following preconditions may be satisfied:

Include at least 40 mL of air in the cell inlet bag.

Table 19 describes the bags of solution that may be attached to each line when performing Load Cells With Uniform Suspension. These solutions and corresponding volumes may be based on the default settings for this task.

TABLE 19

Solutions for Load Cells With Uniform Suspension

| Line | Solution in Bag | Volume (estimation based on factory default values) |
|---|---|---|
| Cell Inlet | Cells | N/A |
| Reagent | None | N/A |
| IC Media | Media with Protein | 0.2 L |
| Wash | None | N/A |
| EC Media | None | N/A |

Load Cells with Uniform Suspension Pathway: Task>Load and Attach>Load Cells with Uniform Suspension Confirm the values for each setting for step 1 shown in Table 20.

TABLE 20

Step 1 Settings for Load Cells With Uniform Suspension

| Setting | Factory Default | Laboratory Default | Modifications |
|---|---|---|---|
| IC Inlet | Cell | | |
| IC Inlet Rate | [50 mL/min] | | 25 mL/min |
| IC Circulation Rate | [200 mL/min] | | 150 mL/min |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | Empty Bag | | |

Confirm the values for each setting for step 2 shown in Table 21.

TABLE 21

Step 2 Settings for Load Cells with Uniform Suspension

| Setting | Factory Default | Laboratory Default | Modifications |
|---|---|---|---|
| IC Inlet | IC Media | | |
| IC Inlet Rate | [50 mL/min] | | 25 mL/min |
| IC Circulation Rate | [200 mL/min] | | 150 mL/min |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | IC Volume (22 mL) | | |

Confirm the values for each setting for step 3 shown in Table 22.

TABLE 22

Step 3 Settings for Load Cells with Uniform Suspension

| Setting | Factory Default | Laboratory Default | Modifications |
|---|---|---|---|
| IC Inlet | None | | |
| IC Inlet Rate | 0 mL/min | | |
| IC Circulation Rate | 200 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | Time (2.0 min) | | |

Day: 0 Bull's Eye Attachment

Purpose: allows adherent cells to attach to the bioreactor membrane while allowing flow on the EC circulation loop. The pump flow rate to the IC loop may be set to zero.

Step 1: Allows cells 7 minutes to attach to the inner surface of the bioreactor at 180°.

Step 2: Circulates the IC fluid and the remaining suspended cells at a high rate in a direction opposite to the initial load.

Step 3: This step is a second 7.0 minute allowance for further cell attachment. Those cells that were relocated from the IC loop or from a different region of the bioreactor will be given a chance to settle and adhere to the bioreactor.

Step 4: Again re-circulates those cells remaining in the IC loop and those cells that have yet to attach to a surface. Circulation may be in the positive direction and the circulation rate may be lower this time to avoid removing those cells that have already attached and to seed preferentially regions of the bioreactor that may not have been seeded in previous steps.

Step 5: This step is a third 7.0 minute allowance for further cell attachment. Those cells that were relocated from the IC loop or from a different region of the bioreactor will be given a chance to settle and adhere to the bioreactor.

Step 6: re-circulates those cells remaining in the IC loop and those cells that have yet to attach to a surface. Circulation may be in the negative direction and the circulation rate is lower this time to avoid removing those cells that have already attached.

Step 7: 24 hour attach cells phase. Cells may have 24 hours to anchor solidly to the bioreactor before feeding begins.

Table 23 describes the bags of solution that may be attached to each line when performing Bull's Eye Attachment. These solutions and corresponding volumes may be based on the default settings for this task.

TABLE 23

Solutions for Bull's Eye Attachment

| Bag | Solution in Bag | Volume (estimation based on factory default values) |
|---|---|---|
| Cell Inlet | None | N/A |
| Reagent | None | N/A |
| IC Media | Media with Protein | 6 mL/hour |
| Wash | None | N/A |
| EC Media | None | N/A |

Bull's Eye Attachment Cells Pathway: Task>Custom>Custom

Enter the values for each setting shown in table 24.

TABLE 24

Step 1 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | |
| EC Inlet | [EC Media] | | |
| EC Inlet Rate | 0.1 mL/min | | |
| EC Circulation Rate | 30 mL/min | | |
| Outlet | EC Outlet | | |
| Rocker Control | [Stationary (0°)] | Stationary (180°) | |
| Stop Condition | Time (7.0 min) | | |

Enter the values for each setting shown in table 25.

TABLE 25

Step 2 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | [0 mL/min] | | −100 mL/min |
| EC Inlet | None | | |
| EC Inlet Rate | 0 mL/min | | |
| EC Circulation Rate | 0 mL/min | | 30 mL/min |
| Outlet | EC Outlet | | |
| Rocker Control | [Stationary] | | In Motion (−90°, 180°, 1 sec) |
| Stop Condition | [Manual] | | Time (2.0 min) |

Enter the values for each setting shown in table 26

TABLE 26

Step 3 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | |

TABLE 26-continued

Step 3 Task Settings for Bull's Eye Attachment

| Setting | Factory Default | Laboratory Default | Modifications |
|---|---|---|---|
| EC Inlet | [EC Media] | IC Media | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Time (7.0 min) | | |

Enter the values for each setting shown in table 27

TABLE 27

Step 4 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | [0 mL/min] | | 50 mL/min |
| EC Inlet | None | | |
| EC Inlet Rate | 0 mL/min | | |
| EC Circulation Rate | [0 mL/min] | | 30 mL/min |
| Outlet | EC Outlet | | |
| Rocker Control | [Stationary] | | In Motion (−90°, 180°, 1 sec) |
| Stop Condition | [Manual] | | Time (4.0 min) |

Enter the values for each setting shown in table 28.

TABLE 28

Step 5 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | |
| EC Inlet | [EC Media] | | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Time (7.0 min) | | |

Enter the values for each setting shown in table 29.

TABLE 29

Step 6 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | [0 mL/min] | | −25 mL/min |
| EC Inlet | None | | |
| EC Inlet Rate | 0 mL/min | | |
| EC Circulation Rate | 0 mL/min | | 30 mL/min |
| Outlet | EC Outlet | | |
| Rocker Control | [Stationary] | | In Motion (−90°, 180°, 1 sec) |
| Stop Condition | [Manual] | | Time (8.0 min) |

Enter the values for each setting shown in table 30.

TABLE 30

Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | |
| EC Inlet | [EC Media] | IC Media | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | [Manual] | | Time (1440.0 min) |

Day: 1 Feed Cells

Purpose: continuously adds a low flow rate to the IC circulation loop and/or the EC circulation loop. There are several outlet settings that can be used to remove the fluid added to the system during this task.

Table 31 describes the bags of solution that may be attached to each line when performing Feed Cells. These solutions and corresponding volumes may be based on the default settings for this task.

TABLE 31

Solutions for Feed Cells

| Bag | Solution in Bag | Volume (estimation based on factory default values) |
|---|---|---|
| Cell Inlet | None | N/A |
| Reagent | None | N/A |
| IC Media | Media with Protein | 6 mL/hour |
| Wash | None | N/A |
| EC Media | None | N/A |

Feed Cells pathway: Task > Feed and Add > Feed Cells

Confirm the values for each setting for step 1 for shown in Table 32.

TABLE 32

Task Settings for Feed Cells

| Setting | Factory Default | Laboratory Default | Modifications |
|---|---|---|---|
| IC Inlet | IC Media | | |
| IC Inlet Rate | 0.1 mL/min | | |
| IC Circulation Rate | 20 mL/min | | |
| EC Inlet | None | | |
| EC Inlet Rate | 0 mL/min | | |
| EC Circulation Rate | 30 mL/min | | |
| Outlet | IC Outlet | | |
| Rocker Control | Stationary (0°) | | |
| Stop Condition | Manual | | |

Increase IC Inlet rate as needed.

Release Adherent Cells and Harvest

Purpose: releases cells from the membrane, leaving the cells in the IC loop and transfers cells in suspension from the IC circulation loop, including cells in the bioreactor, into the harvest bag.

Step 1: performs the IC EC Washout task in preparation for adding a reagent. For example, the system replaces IC EC media with PBS to remove protein, Ca++, and Mg++ in preparation for adding trypsin.

Step 2: loads a reagent into the system until the bag is empty.
Step 3: chases the reagent into the IC loop.
Step 4: mixes the reagent within the IC loop.
Step 5: transfers cells in suspension from the IC circulation loop, including cells in the bioreactor, to the harvest bag.

Before starting this task, the following preconditions may be satisfied:
Include at least 40 mL of air on the cell inlet bag.
Table 33 describes the bags of solution that may be attached to each line when performing Release Adherent Cells And Harvest. These solutions and corresponding volumes may be based on the default settings for this task.

TABLE 33

Solutions for Release Adherent Cells And Harvest

| Bag | Solution in Bag | Volume (estimation based on factory default values) |
|---|---|---|
| Cell Inlet | None | N/A |
| Reagent | Trypsin | 180 mL |
| IC Media | Media with Protein | 0.6 L |
| Wash | PBS | 1.4 L |
| EC Media | None | N/A |

Release Adherent Cells Pathway: Task>Release and Harvest>Release Adherent Cells and Harvest Confirm the values for each setting for step 1 shown in Table 34.

TABLE 34

Step 1 Settings for Release Adherent Cells And Harvest

| Setting | Factory Default | Laboratory Default | Modifications |
|---|---|---|---|
| IC Inlet | Wash | | |
| IC Inlet Rate | 100 mL/mm | | |
| IC Circulation Rate | -17 mL/min | | |
| EC Inlet | Wash | | |
| EC Inlet Rate | 148 mL/min | | |
| EC Circulation Rate | -1.7 mL/min | | |
| Outlet | IC and EC Outlet | | |
| Rocker Control | In Motion (-90°, 180°, 1 sec) | | |
| Stop Condition | Exchange (2.5 IC Volumes) (2.5 EC Volumes) | | |

Confirm the values for each setting for step 2 shown in Table 35.

TABLE 35

Step 2 Settings for Release Adherent Cells And Harvest

| Setting | Factory Default | Laboratory Default | Modifications |
|---|---|---|---|
| IC Inlet | Reagent | | |
| IC Inlet Rate | 50 mL/min | | |
| IC Circulation Rate | 300 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | In Motion (-90°, 180°, 1 sec) | | |
| Stop Condition | Empty Bag | | |

Confirm the values for each setting for step 3 shown in Table 36.

TABLE 36

Step 3 Settings for Release Adherent Cells And Harvest

| Setting | Factory Default | Laboratory Default | Modifications |
|---|---|---|---|
| IC Inlet | Wash | | |
| IC Inlet Rate | 50 mL/min | | |
| IC Circulation Rate | 300 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | IC Volume (22 mL) | | |

Confirm the values for each setting for step 4 shown in Table 37.

TABLE 37

Step 4 Settings for Release Adherent Cells And Harvest

| Setting | Factory Default | Laboratory Default | Modifications |
|---|---|---|---|
| IC Inlet | None | | |
| IC Inlet Rate | 0 mL/min | | |
| IC Circulation Rate | 300 mL/min | | |
| EC Inlet | None | | |
| EC Inlet Rate | 0 mL/min | | |
| EC Circulation Rate | 30 mL/min | | |

TABLE 37-continued

Step 4 Settings for Release Adherent Cells And Harvest

| Setting | Factory Default | Laboratory Default | Modifications |
|---|---|---|---|
| Outlet | EC Outlet | | |
| Rocker Control | In Motion (−90°, 180°, 1 sec) | | |
| Stop Condition | Time (4 min) | | |

Confirm the values for each setting for step 5 shown in Table 38.

TABLE 38

Step 5 Settings for Release Adherent Cells And Harvest

| Setting | Factory Default | Laboratory Default | Modifications |
|---|---|---|---|
| IC Inlet | IC Media | | |
| IC Inlet Rate | 400 mL/min | | |
| IC Circulation Rate | −70 mL/min | | |
| EC Inlet | [EC Media] | IC Media | |
| EC Inlet Rate | 60 mL/min | | |
| EC Circulation Rate | 30 mL/min | | |
| Outlet | Harvest | | |
| Rocker Control | In Motion (−90°, 180°, 1 sec) | | |
| Stop Condition | IC Volume (378 mL) | | |

The results of the study may be as follows:

TABLE 39

| Load | Time (days) | #Cells Loaded | #Cells Harvested | Viability | Agg (0-5) | 69% Adjusted Doubling Time (Hrs) | Unadjusted Doubling Time (Hrs) | Mean Flask Doubling Time (Hrs) |
|---|---|---|---|---|---|---|---|---|
| BullsEye | 4.8 | 1.52E+06 | 1.97E+08 | 98.1% | 2 | 27.2 | 31.2 | 24.1 |
| BullsEye | 4.8 | 1.52E+06 | 2.05E+08 | 98.0% | 2 | 26.8 | 30.7 | 24.1 |
| BullsEye | 4.8 | 1.52E+06 | 2.01E+08 | 99.3% | 2 | 27.1 | 31.0 | 24.1 |
| Control | 4.8 | 1.52E+06 | 1.38E+08 | 99.3% | 2 | 31.0 | 36.2 | 24.1 |

The Bull's Eye load may be evaluated using MSC from four different donors. Yields from Bull's Eye loaded harvests may be consistently higher than the yields loaded using LCWUS and cultured under identical conditions. The mean cell yield increase using Bull's Eye (n=6) vs. LCWUS (n=4) may be 25%.

Viability of MSC samples from the IC loop taken immediately after performing the Bull's Eye load may be 100%. Viability of MSC from Bull's Eye harvests may be over 98% for all samples. MSC from Bull's Eye harvests may display typical morphology in culture, and all MSC biomarkers measured by flow cytometry may conform to ISCT standards.

Example 3

The same protocol as described above with respect to Example 2 may be used to study modifications to the Bulls Eye attachment protocol. The modifications to the Bulls Eye attachment (Bulls Eye II), and to the protocol described above, include eliminating the attachments phases after the circulation rates: 100 ml/min; −50 ml/min; and 25 ml/min. That is, instead of having 7 minute stop conditions as described above, there is no stop condition so that the next circulation rate follows the previous circulation rate. A control, as well as an original Bulls Eye run (Bulls Eye I) may also be performed as a comparison.

The results of this study may be as follows:

TABLE 40

| Load | Time (days) | #Cells Loaded | #Cells Harvested | Viability | Agg (0-5) | 69% Adjusted Doubling Time (Hrs) | Unadjusted Doubling Time (Hrs) | Mean Flask Doubling Time (Hrs) |
|---|---|---|---|---|---|---|---|---|
| BullsEye I | 4.9 | 1.52E+07 | 2.60E+08 | 99.2% | 0 | 25.4 | 28.7 | 26.0 (500 cells/cm2) |
| Control | 4.9 | 1.52E+07 | 1.94E+08 | 97.5% | 1 | 27.9 | 32.0 | 25.5 (345 cells/cm2) |
| BullsEye II | 4.9 | 1.52E+07 | 2.10E+08 | 98.1% | 1 | 27.2 | 31.1 | ? |
| BullsEye II | 4.9 | 1.52E+07 | 2.07E+08 | 98.7% | 1 | 27.3 | 31.2 | ? |

Various components may be referred to herein as "operably associated." As used herein, "operably associated" refers to components that are linked together in operable fashion, and encompasses embodiments in which components are linked directly, as well as embodiments in which additional components are placed between the two linked components.

The foregoing discussion of the one or more embodiments of the present invention has been presented for purposes of illustration and description. The foregoing is not intended to be limiting. In the foregoing Detailed Description for example, various features of the one or more embodiments may have been grouped together for the purpose of streamlining the disclosure. This method of disclosure is not to be interpreted as reflecting an intention that the embodiments require more features than may be expressly recited in a claim. Rather, as the following claims reflect, inventive aspects may lie in less than all features of a single foregoing disclosed embodiment. Thus, the following claims are hereby incorporated into this Detailed Description, with each claim standing on its own as a separate embodiment of the present invention.

Moreover, though the description includes description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

We claim:

1. A method of growing cells in a cell expansion system, the method comprising:
    circulating fluid, with a pump, through a bioreactor comprising a hollow fiber membrane with a plurality of hollow fibers, wherein the fluid comprises a plurality of cells and the fluid enters the bioreactor through a first inlet and exits the bioreactor through a first outlet;
    reducing the rate of circulating fluid by reducing a flow rate of the pump;
    maintaining the bioreactor in a first horizontal orientation for a first predetermined period of time to allow at least a first portion of the plurality of cells to settle and attach to a first portion of at least one of the plurality of hollow fibers;
    after the first predetermined period of time, rotating, with a rotational device, the bioreactor to a second horizontal orientation that is about 180 degrees from the first horizontal orientation; and
    after the rotating, expanding at least the first portion of the plurality of cells attached to the first portion of the at least one of the plurality of hollow fibers while the bioreactor is oriented in the second horizontal orientation by feeding the portion of cells and growing the portion of cells downward in the bioreactor under an influence of gravity toward a portion of the at least one of the plurality of hollow fibers that does not have attached cells.

2. The method of claim 1, wherein the first predetermined period of time is long enough to allow the portion of cells to attach and expand.

3. The method of claim 2, wherein the first predetermined period of time is greater than about 10 hours.

4. The method of claim 1, wherein the first predetermined period of time is less than about 8 minutes.

5. The method of claim 4, wherein the first predetermined period of time is about 5 minutes.

6. The method of claim 1, further comprising:
    after the first predetermined period of time and before rotating the bioreactor to a second horizontal orientation:
        rotating the bioreactor to a first vertical orientation and maintaining the bioreactor in the first vertical orientation for a second predetermined period of time; and
        after the second predetermined period of time, rotating the bioreactor to a second vertical orientation that is about 180 degrees from the first vertical orientation and maintaining the bioreactor in the second vertical orientation for a third predetermined period of time.

7. The method of claim 6, wherein the second predetermined period of time is of sufficient duration to allow the portion of cells to expand.

8. The method of claim 7, wherein the third predetermined period of time is equal in duration to the second period of time.

9. The method of claim 7, wherein the second predetermined period of time is at least about 10 hours.

10. The method of claim 1, wherein the plurality of cells comprises stem cells.

11. The method of claim 10, wherein the stem cells comprise mesenchymal stem cells.

12. The method of claim 1, wherein the plurality of cells comprises one or more cells from the group consisting of: fibroblasts, keratinocytes, progenitor, endothelial, or combinations thereof.

13. The method of claim 1, wherein the first portion comprises an inside surface of the at least one of the plurality of hollow fibers.

14. The method of claim 13, wherein the second portion comprises a different portion of the inside surface of the at least one of the plurality of hollow fibers.

15. The method of claim 1, wherein the first predetermined period of time is long enough to allow the portion of cells to attach.

* * * * *